(12) United States Patent
Landvik et al.

(10) Patent No.: US 7,871,800 B2
(45) Date of Patent: Jan. 18, 2011

(54) POLYPEPTIDES HAVING GLUCOAMYLASE ACTIVITY AND POLYNUCLEOTIDES ENCODING SAME

(75) Inventors: Sara Landvik, Vedbaek (DK); Jiyin Liu, Raleigh, NC (US); Carsten Horslev Hansen, Vaerloese (DK); Chee Leong Soong, Raleigh, NC (US); Jeppe Wegener Tams, Gentofte (DK)

(73) Assignees: Novozymes A/S, Bagsvaerd (DK); Novozymes North America, Inc., Franklinton, NC (US)

( * ) Notice: Subject to any disclaimer, the term of this patent is extended or adjusted under 35 U.S.C. 154(b) by 0 days.

(21) Appl. No.: 12/529,582

(22) PCT Filed: Apr. 13, 2007

(86) PCT No.: PCT/US2007/066618

§ 371 (c)(1),
(2), (4) Date: Sep. 2, 2009

(87) PCT Pub. No.: WO2007/124285

PCT Pub. Date: Nov. 1, 2007

(65) Prior Publication Data

US 2010/0120108 A1    May 13, 2010

Related U.S. Application Data

(60) Provisional application No. 60/793,128, filed on Apr. 19, 2006.

(51) Int. Cl.
C12P 19/20        (2006.01)
C12P 1/00         (2006.01)
C12N 9/34         (2006.01)
A61K 38/00        (2006.01)

(52) U.S. Cl. .................. 435/96; 435/205; 435/200; 435/267; 530/300

(58) Field of Classification Search ................ None
See application file for complete search history.

(56) References Cited

U.S. PATENT DOCUMENTS 4,727,046 A    2/1988    Tuntasood et al.

FOREIGN PATENT DOCUMENTS

| WO | WO 84/02921    | 8/1984  |
|----|----------------|---------|
| WO | WO 99/28248    | 6/1999  |
| WO | WO 00/75296    | 12/2000 |
| WO | WO 2004/111218 | 12/2004 |
| WO | WO 2005/069840 | 8/2005  |
| WO | WO 2006/069289 | 6/2006  |

OTHER PUBLICATIONS

Boel et al., The EMBO Journal, vol. 3, No. 5, pp. 1097-1102 (1984).
Zhao et al., Applied and Environmental Microbiology, vol. 66, No. 6, pp. 2531-2535 (2000).

*Primary Examiner*—Nashaat T Nashed
(74) *Attorney, Agent, or Firm*—Elias J. Lambiris

(57) ABSTRACT

The present invention relates to polypeptides having glucoamylase activity and isolated polynucleotides encoding said polypeptides preferably derived from a strain of *Peniphora rufomarginata*. The invention also relates to nucleic acid constructs, vectors, and host cells comprising the polynucleotides as well as methods for producing and using the polypeptides. The invention also relates to the composition comprising a glucoamylase of the invention as well as the use such compositions for starch conversion processes, brewing, including processes for producing fermentation products or syrups.

35 Claims, No Drawings

SEQUENCE LISTING

```
<160> NUMBER OF SEQ ID NOS: 21

<210> SEQ ID NO 1
<211> LENGTH: 2304
<212> TYPE: DNA
<213> ORGANISM: Peniophora rufomaginata
<220> FEATURE:
<221> NAME/KEY: CDS
<222> LOCATION: (1)..(156)
<220> FEATURE:
<221> NAME/KEY: misc_feature
<222> LOCATION: (1)..(2304)
<223> OTHER INFORMATION: Genomic DNA
<220> FEATURE:
<221> NAME/KEY: misc_signal
<222> LOCATION: (1)..(61)
<220> FEATURE:
<221> NAME/KEY: mat_peptide
<222> LOCATION: (61)..(2301)
<220> FEATURE:
<221> NAME/KEY: Intron
<222> LOCATION: (157)..(212)
<220> FEATURE:
<221> NAME/KEY: CDS
<222> LOCATION: (213)..(287)
<220> FEATURE:
<221> NAME/KEY: Intron
<222> LOCATION: (288)..(358)
<220> FEATURE:
<221> NAME/KEY: CDS
<222> LOCATION: (359)..(499)
<220> FEATURE:
<221> NAME/KEY: Intron
<222> LOCATION: (500)..(552)
<220> FEATURE:
<221> NAME/KEY: CDS
<222> LOCATION: (553)..(643)
<220> FEATURE:
<221> NAME/KEY: Intron
<222> LOCATION: (644)..(690)
<220> FEATURE:
<221> NAME/KEY: CDS
<222> LOCATION: (691)..(777)
<220> FEATURE:
<221> NAME/KEY: Intron
```

```
<222> LOCATION: (778)..(833)
<220> FEATURE:
<221> NAME/KEY: CDS
<222> LOCATION: (834)..(1288)
<220> FEATURE:
<221> NAME/KEY: Intron
<222> LOCATION: (1289)..(1343)
<220> FEATURE:
<221> NAME/KEY: CDS
<222> LOCATION: (1344)..(1648)
<220> FEATURE:
<221> NAME/KEY: Intron
<222> LOCATION: (1649)..(1705)
<220> FEATURE:
<221> NAME/KEY: CDS
<222> LOCATION: (1706)..(1877)
<220> FEATURE:
<221> NAME/KEY: Intron
<222> LOCATION: (1878)..(1937)
<220> FEATURE:
<221> NAME/KEY: CDS
<222> LOCATION: (1938)..(2043)
<220> FEATURE:
<221> NAME/KEY: Intron
<222> LOCATION: (2044)..(2097)
<220> FEATURE:
<221> NAME/KEY: CDS
<222> LOCATION: (2098)..(2157)
<220> FEATURE:
<221> NAME/KEY: Intron
<222> LOCATION: (2158)..(2215)
<220> FEATURE:
<221> NAME/KEY: CDS
<222> LOCATION: (2216)..(2301)

<400> SEQUENCE: 1 atg cgt ctc cca caa ctt gga gtc atc ggt gca gcc ttt ttc gcc gct      48
Met Arg Leu Pro Gln Leu Gly Val Ile Gly Ala Ala Phe Phe Ala Ala
-20             -15                 -10                 -5 tcg gcg gtc gcc cag gtc gac tcg tac gtc gcg agc gag ggt ccc atc      96
Ser Ala Val Ala Gln Val Asp Ser Tyr Val Ala Ser Glu Gly Pro Ile
            -1  1               5                  10 gca aaa gca gga ctc ttc gcc aac atc ggt cct gac ggc tcc aag gat     144
Ala Lys Ala Gly Leu Phe Ala Asn Ile Gly Pro Asp Gly Ser Lys Asp
        15                  20                  25 gct ggc gct ggg gtaaggacac tgccattcga atccctctac ccttgagcta         196
Ala Gly Ala Gly
        30 acgcttagct tgacag gcg ggt ttg gtg aca gcg tct ccc tcg acg tcg aac   248
               Ala Gly Leu Val Thr Ala Ser Pro Ser Thr Ser Asn
                           35                  40 ccg gac tat gca tac aca tgg acc cgt gac agc agc ctt gtatttaaag      297
Pro Asp Tyr Ala Tyr Thr Trp Thr Arg Asp Ser Ser Leu
45                  50                  55 tcattgccac tcctctcggc tatattacca gctgtctgac caggcatctg tatattcgta   357 g gcc atc atc gac cag tac acc ctc ggt atc gac act tcg act ggc agc   406
  Ala Ile Ile Asp Gln Tyr Thr Leu Gly Ile Asp Thr Ser Thr Gly Ser
        60                  65                  70 cac atc aat gac ttc ttc acc gcc gaa gcc aga ctt caa caa gtt tcc     454
His Ile Asn Asp Phe Phe Thr Ala Glu Ala Arg Leu Gln Gln Val Ser
        75                  80                  85 aac ccg tct ggt act gtg tct tcc ggc gga ctt ggc gag ccg aag         499
Asn Pro Ser Gly Thr Val Ser Ser Gly Gly Leu Gly Glu Pro Lys
90                  95                  100 gtaatggtag cgccgccttc gctttcagtt gcgacactaa tgcaagctct cag ttc      555
                                                         Phe
                                                         105
```

```
aac ctt gac ttc agc gcg ttc act ggc gcc tgg gga cgt cct cag cgt      603
Asn Leu Asp Phe Ser Ala Phe Thr Gly Ala Trp Gly Arg Pro Gln Arg
            110                 115                 120 gat ggc cct gct ctg cgt tcc aca act ttg atc aca tgg g gtatgcgtgt     653
Asp Gly Pro Ala Leu Arg Ser Thr Thr Leu Ile Thr Trp
    125                 130 tctccatctg tcctgcccgt cggctcatca tgagcag gg  aac tac ctc tac agc     707
                                            Gly Asn Tyr Leu Tyr Ser
                                                                140 agt gga aac acg act ttt gtc acg aac acg ctc tgg ccc gta atc aag      755
Ser Gly Asn Thr Thr Phe Val Thr Asn Thr Leu Trp Pro Val Ile Lys
            145                 150                 155 ctt gat ctc gat tat gtc gtt g gtcaggaact gttctcattg cttttgactt       807
Leu Asp Leu Asp Tyr Val Val
            160 gatctaatgt aaattgtgct ccctag cg  gac tgg aac cag aca acc ttc gat     859
                                Ala Asp Trp Asn Gln Thr Thr Phe Asp
                                    165                 170 ctc tgg gag gag gtt tct tcg tcc tcg ttc ttt gcc act gcc gtc cag      907
Leu Trp Glu Glu Val Ser Ser Ser Ser Phe Phe Ala Thr Ala Val Gln
            175                 180                 185 cat cgc tct ctg cgt gag ggc gcc gct ttc gct acc ctc gtc ggc gac      955
His Arg Ser Leu Arg Glu Gly Ala Ala Phe Ala Thr Leu Val Gly Asp
            190                 195                 200 agt acc tcg gcc tcc acg tat act acg cag gcc gcg aac gtg ctc tgc     1003
Ser Thr Ser Ala Ser Thr Tyr Thr Thr Gln Ala Ala Asn Val Leu Cys
205             210                 215                 220 ttc ttg cag tcg tac tgg aac ccc acg ggc ggc tac att acc gcg aac     1051
Phe Leu Gln Ser Tyr Trp Asn Pro Thr Gly Gly Tyr Ile Thr Ala Asn
            225                 230                 235 acg ggc ggt gga cgc agc gga aag gac gct aac acg gtt ctc gcc tcg     1099
Thr Gly Gly Gly Arg Ser Gly Lys Asp Ala Asn Thr Val Leu Ala Ser
            240                 245                 250 att cac acc tgg gac atc aag gcc ggc tgc gac gct gct acg ttc cag     1147
Ile His Thr Trp Asp Ile Lys Ala Gly Cys Asp Ala Ala Thr Phe Gln
            255                 260                 265 cca tgc tca gac aag gcg ctc tcg aac ctc aag gtt tac gct gac gct     1195
Pro Cys Ser Asp Lys Ala Leu Ser Asn Leu Lys Val Tyr Ala Asp Ala
            270                 275                 280 ttc cgc tcc atc tat tcc atc aat agc ggt atc gca gcc tct gcc gct     1243
Phe Arg Ser Ile Tyr Ser Ile Asn Ser Gly Ile Ala Ala Ser Ala Ala
285             290                 295                 300 gtc gcc acc ggg cgc tac cct gaa gac agc tac tac aac ggc aac         1288
Val Ala Thr Gly Arg Tyr Pro Glu Asp Ser Tyr Tyr Asn Gly Asn
            305                 310                 315 gtatgcatta tcttttctct atacgttgac gtctccacct catgcatctt tgcag cct    1346
                                                               Pro tgg tac ctc act act ctc gct ccg gct gag cag ctc tac gac gca ctt     1394
Trp Tyr Leu Thr Thr Leu Ala Pro Ala Glu Gln Leu Tyr Asp Ala Leu
            320                 325                 330 acc act tgg gac tcg gtc ggc tca atc aat gtc acg agt act tcc ctg     1442
Thr Thr Trp Asp Ser Val Gly Ser Ile Asn Val Thr Ser Thr Ser Leu
            335                 340                 345 gcg ttc tgg cag caa ctc gac tcg agc gtc gct gtt ggc tcc tat gcg     1490
Ala Phe Trp Gln Gln Leu Asp Ser Ser Val Ala Val Gly Ser Tyr Ala
            350                 355                 360 aag tcc tcg acc acc tac gca acg ctc acc gcg gct gtc aag acg ttc     1538
Lys Ser Ser Thr Thr Tyr Ala Thr Leu Thr Ala Ala Val Lys Thr Phe
365             370                 375                 380
```

-continued

```
gct gac ggc ttc gtc tcg gta gtc cag aag tac acc ccc tcc tct ggc    1586
Ala Asp Gly Phe Val Ser Val Val Gln Lys Tyr Thr Pro Ser Ser Gly
                385                 390                 395 gcg ctc tct gag cag ttc gac aag tcc act gga gct cag acc tct gct    1634
Ala Leu Ser Glu Gln Phe Asp Lys Ser Thr Gly Ala Gln Thr Ser Ala
            400                 405                 410 gtt gat ctc aca tg gtgagcttgg gcgcactatc acttcctttg aacaaagacg     1688
Val Asp Leu Thr Trp
        415 cttacgtcga tccgcag g tcg tat gct tca gct atc act gct ttc gag gct   1739
                    Ser Tyr Ala Ser Ala Ile Thr Ala Phe Glu Ala
                                420                 425 cgt aac gga acg acc ccg act tct tgg ggc gcg gct ggt ctg att gtt    1787
Arg Asn Gly Thr Thr Pro Thr Ser Trp Gly Ala Ala Gly Leu Ile Val
    430                 435                 440 cct tca acc tgc tcg acc tcc gga ggt ggc agt ggc ggc ggc agt ggt    1835
Pro Ser Thr Cys Ser Thr Ser Gly Gly Gly Ser Gly Gly Gly Ser Gly
445                 450                 455                 460 ggc agc acc gtc gct gta acc ttc aac gtt cag gct acc acc             1877
Gly Ser Thr Val Ala Val Thr Phe Asn Val Gln Ala Thr Thr
                465                 470 gtaagcactc tttccgtatg tttcgaagtg tccatatgaa ggcctcgtca tcgtcactag   1937 gtc ttc ggc gag aac atc tac atc acc ggt agc gtg gat gcc ttg gag    1985
Val Phe Gly Glu Asn Ile Tyr Ile Thr Gly Ser Val Asp Ala Leu Glu
475                 480                 485                 490 gac tgg agc ccg gac aac gcc ctg ctg ctc tcc tcg gcc aac tac cct    2033
Asp Trp Ser Pro Asp Asn Ala Leu Leu Leu Ser Ser Ala Asn Tyr Pro
                495                 500                 505 acc tgg agt a gtgcgtgctt acgtcttcat ctcatgtgct catcatattg          2083
Thr Trp Ser actatcgcgt atag tc acc gtg aac ctg ccg gcg tcg act tcc gtg cag     2132
                Ile Thr Val Asn Leu Pro Ala Ser Thr Ser Val Gln
                                515                 520 tac aag tac atc cgc aag aac aat g gtgagatctt atcgatctgt            2177
Tyr Lys Tyr Ile Arg Lys Asn Asn
                525 acgttacccc taaagctcac gcgtgatcac tctccaag gt gcc gcc atc acc tgg   2232
                                           Gly Ala Ala Ile Thr Trp
                                                           535 gag tcg gac ccg aac atc cag atc aca acc ccg gcc tca ggc acg tat    2280
Glu Ser Asp Pro Asn Ile Gln Ile Thr Thr Pro Ala Ser Gly Thr Tyr
                540                 545                 550 act gcc aac gat tcc tgg cgc tag                                    2304
Thr Ala Asn Asp Ser Trp Arg
            555
```

<210> SEQ ID NO 2
<211> LENGTH: 578
<212> TYPE: PRT
<213> ORGANISM: Peniophora rufomaginata

<400> SEQUENCE: 2

```
Met Arg Leu Pro Gln Leu Gly Val Ile Gly Ala Ala Phe Phe Ala Ala
-20                 -15                 -10                 -5

Ser Ala Val Ala Gln Val Asp Ser Tyr Val Ala Ser Glu Gly Pro Ile
            -1  1                 5                  10

Ala Lys Ala Gly Leu Phe Ala Asn Ile Gly Pro Asp Gly Ser Lys Asp
        15                  20                  25

Ala Gly Ala Gly Ala Gly Leu Val Thr Ala Ser Pro Ser Thr Ser Asn
```

```
                30                  35                  40
Pro Asp Tyr Ala Tyr Thr Trp Thr Arg Asp Ser Ser Leu Ala Ile Ile
45                  50                  55                  60

Asp Gln Tyr Thr Leu Gly Ile Asp Thr Ser Thr Gly Ser His Ile Asn
                65                  70                  75

Asp Phe Phe Thr Ala Glu Ala Arg Leu Gln Gln Val Ser Asn Pro Ser
                80                  85                  90

Gly Thr Val Ser Ser Gly Gly Leu Gly Glu Pro Lys Phe Asn Leu Asp
                95                 100                 105

Phe Ser Ala Phe Thr Gly Ala Trp Gly Arg Pro Gln Arg Asp Gly Pro
110                 115                 120

Ala Leu Arg Ser Thr Thr Leu Ile Thr Trp Gly Asn Tyr Leu Tyr Ser
125                 130                 135                 140

Ser Gly Asn Thr Thr Phe Val Thr Asn Thr Leu Trp Pro Val Ile Lys
                145                 150                 155

Leu Asp Leu Asp Tyr Val Val Ala Asp Trp Asn Gln Thr Thr Phe Asp
                160                 165                 170

Leu Trp Glu Glu Val Ser Ser Ser Phe Phe Ala Thr Ala Val Gln
                175                 180                 185

His Arg Ser Leu Arg Glu Gly Ala Ala Phe Ala Thr Leu Val Gly Asp
                190                 195                 200

Ser Thr Ser Ala Ser Thr Tyr Thr Thr Gln Ala Ala Asn Val Leu Cys
205                 210                 215                 220

Phe Leu Gln Ser Tyr Trp Asn Pro Thr Gly Gly Tyr Ile Thr Ala Asn
                225                 230                 235

Thr Gly Gly Gly Arg Ser Gly Lys Asp Ala Asn Thr Val Leu Ala Ser
                240                 245                 250

Ile His Thr Trp Asp Ile Lys Ala Gly Cys Asp Ala Ala Thr Phe Gln
                255                 260                 265

Pro Cys Ser Asp Lys Ala Leu Ser Asn Leu Lys Val Tyr Ala Asp Ala
270                 275                 280

Phe Arg Ser Ile Tyr Ser Ile Asn Ser Gly Ile Ala Ala Ser Ala Ala
285                 290                 295                 300

Val Ala Thr Gly Arg Tyr Pro Glu Asp Ser Tyr Tyr Asn Gly Asn Pro
                305                 310                 315

Trp Tyr Leu Thr Thr Leu Ala Pro Ala Glu Gln Leu Tyr Asp Ala Leu
                320                 325                 330

Thr Thr Trp Asp Ser Val Gly Ser Ile Asn Val Thr Ser Thr Ser Leu
                335                 340                 345

Ala Phe Trp Gln Gln Leu Asp Ser Ser Val Ala Val Gly Ser Tyr Ala
350                 355                 360

Lys Ser Ser Thr Thr Tyr Ala Thr Leu Thr Ala Ala Val Lys Thr Phe
365                 370                 375                 380

Ala Asp Gly Phe Val Ser Val Val Gln Lys Tyr Thr Pro Ser Ser Gly
                385                 390                 395

Ala Leu Ser Glu Gln Phe Asp Lys Ser Thr Gly Ala Gln Thr Ser Ala
                400                 405                 410

Val Asp Leu Thr Trp Ser Tyr Ala Ser Ala Ile Thr Ala Phe Glu Ala
                415                 420                 425

Arg Asn Gly Thr Thr Pro Thr Ser Trp Gly Ala Ala Gly Leu Ile Val
                430                 435                 440

Pro Ser Thr Cys Ser Thr Ser Gly Gly Gly Ser Gly Gly Gly Ser Gly
445                 450                 455                 460
```

```
Gly Ser Thr Val Ala Val Thr Phe Asn Val Gln Ala Thr Thr Val Phe
                465                 470                 475
Gly Glu Asn Ile Tyr Ile Thr Gly Ser Val Asp Ala Leu Glu Asp Trp
            480                 485                 490
Ser Pro Asp Asn Ala Leu Leu Leu Ser Ser Ala Asn Tyr Pro Thr Trp
        495                 500                 505
Ser Ile Thr Val Asn Leu Pro Ala Ser Thr Ser Val Gln Tyr Lys Tyr
    510                 515                 520
Ile Arg Lys Asn Asn Gly Ala Ala Ile Thr Trp Glu Ser Asp Pro Asn
525                 530                 535                 540
Ile Gln Ile Thr Thr Pro Ala Ser Gly Thr Tyr Thr Ala Asn Asp Ser
                545                 550                 555
Trp Arg

<210> SEQ ID NO 3
<211> LENGTH: 1737
<212> TYPE: DNA
<213> ORGANISM: Peniophora rufomaginata
<220> FEATURE:
<221> NAME/KEY: misc_feature
<222> LOCATION: (1)..(1737)
<223> OTHER INFORMATION: CDNA

<400> SEQUENCE: 3
atgcgtctcc cacaacttgg agtcatcggt gcagccttt tcgccgcttc ggcggtcgcc      60
caggtcgact cgtacgtcgc gagcgagggt cccatcgcaa aagcaggact cttcgccaac     120
atcggtcctg acggctccaa ggatgctggc gctggggcgg gtttggtgac agcgtctccc     180
tcgacgtcga acccggacta tgcatacaca tggacccgtg acagcagcct tgccatcatc     240
gaccagtaca ccctcggtat cgacacttcg actggcagcc acatcaatga cttcttcacc     300
gccgaagcca gacttcaaca gtttccaacc cgtctggta ctgtgtcttc ggcggactt       360 ggcgagccga agttcaacct tgacttcagc gcgttcactg gcgcctgggg acgtcctcag     420
cgtgatggcc ctgctctgcg ttccacaact ttgatcacat gggggaacta cctctacagc     480
agtggaaaca cgacttttgt cacgaacacg ctctggcccg taatcaagct tgatctcgat     540
tatgtcgttg cggactggaa ccagacaacc ttcgatctct gggaggaggt ttcttcgtcc     600
tcgttctttg ccactgccgt ccagcatcgc tctctgcgtg agggcgccgc tttcgctacc     660
ctcgtcggcg acagtacctc ggcctccacg tatactacgc aggccgcgaa cgtgctctgc     720
ttcttgcagt cgtactggaa ccccacgggc ggctacatta ccgcgaacac gggcggtgga     780
cgcagcggaa aggacgctaa cacggttctc gcctcgattc acacctggga catcaaggcc     840
ggctgcgacg ctgctacgtt ccagccatgc tcagacaagg cgctctcgaa cctcaaggtt     900
tacgctgacg ctttccgctc catctattcc atcaatagcg gtatcgcagc ctctgccgct     960
gtcgccaccg ggcgctaccc tgaagacagc tactacaacg caaccccttg gtacctcact    1020
actctcgctc cggctgagca gctctacgac gcacttacca cttgggactc ggtcggctca    1080
atcaatgtca cgagtacttc cctggcgttc tggcagcaac tcgactcgag cgtcgctgtt    1140
ggctcctatg cgaagtcctc gaccacctac gcaacgctca ccgcggctgt caagacgttc    1200
gctgacggct tcgtctcggt agtccagaag tacacgccct cctctggcgc gctctctgag    1260
cagttcgaca gtccactgg agctcagacc tctgctgttg atctcacatg gtcgtatgct    1320
tcagctatca ctgctttcga ggctcgtaac ggaacgaccc cgacttcttg gggcgcggct    1380
```

-continued

```
ggtctgattg ttccttcaac ctgctcgacc tccggaggtg gcagtggcgg cggcagtggt    1440
ggcagcaccg tcgctgtaac cttcaacgtt caggctacca ccgtcttcgg cgagaacatc    1500
tacatcaccg gtagcgtgga tgccttggag gactggagcc cggacaacgc cctgctgctc    1560
tcctcggcca actaccctac ctggagtatc accgtgaacc tgccggcgtc gacttccgtg    1620
cagtacaagt acatccgcaa gaacaatggt gccgccatca cctgggagtc ggacccgaac    1680
atccagatca caaccccggc ctcaggcacg tatactgcca acgattcctg cgcctag      1737
```

<210> SEQ ID NO 4
<211> LENGTH: 31
<212> TYPE: PRT
<213> ORGANISM: Aspergillus kawachii
<220> FEATURE:
<221> NAME/KEY: MISC_FEATURE
<222> LOCATION: (1)..(31)
<223> OTHER INFORMATION: Aspergillus kawachii linker

<400> SEQUENCE: 4

Thr Thr Thr Thr Thr Thr Ala Ala Ala Thr Ser Thr Ser Lys Ala Thr
1               5                   10                  15

Thr Ser Ser Ser Ser Ser Ser Ala Ala Ala Thr Thr Ser Ser Ser
            20                  25                  30

<210> SEQ ID NO 5
<211> LENGTH: 1350
<212> TYPE: DNA
<213> ORGANISM: Rhizomucor pusillus
<220> FEATURE:
<221> NAME/KEY: CDS
<222> LOCATION: (1)..(1350)
<223> OTHER INFORMATION: Catalytic domain

<400> SEQUENCE: 5

```
agc cct ttg ccc caa cag cag cga tat ggc aaa aga gca act tcg gat       48
Ser Pro Leu Pro Gln Gln Gln Arg Tyr Gly Lys Arg Ala Thr Ser Asp
1               5                   10                  15 gac tgg aaa ggc aag gcc att tat cag ctg ctt aca gat cga ttt ggc       96
Asp Trp Lys Gly Lys Ala Ile Tyr Gln Leu Leu Thr Asp Arg Phe Gly
            20                  25                  30 cgc gcc gat gac tca aca agc aac tgc tct aat tta tcc aac tac tgt     144
Arg Ala Asp Asp Ser Thr Ser Asn Cys Ser Asn Leu Ser Asn Tyr Cys
        35                  40                  45 ggt ggt acc tac gaa ggc att acg aag cat ctt gac tac att tcc ggt     192
Gly Gly Thr Tyr Glu Gly Ile Thr Lys His Leu Asp Tyr Ile Ser Gly
    50                  55                  60 atg ggc ttt gat gct atc tgg ata tcg cca att ccc aag aac tcg gat     240
Met Gly Phe Asp Ala Ile Trp Ile Ser Pro Ile Pro Lys Asn Ser Asp
65                  70                  75                  80 gga ggc tac cac ggc tac tgg gct aca gat ttc tac caa cta aac agc     288
Gly Gly Tyr His Gly Tyr Trp Ala Thr Asp Phe Tyr Gln Leu Asn Ser
                85                  90                  95 aac ttt ggt gat gaa tcc cag ctc aaa gcg ctc atc cag gct gcc cat     336
Asn Phe Gly Asp Glu Ser Gln Leu Lys Ala Leu Ile Gln Ala Ala His
            100                 105                 110 gaa cgt gac atg tat gtt atg ctt gat gtc gta gcc aat cat gca ggt     384
Glu Arg Asp Met Tyr Val Met Leu Asp Val Val Ala Asn His Ala Gly
        115                 120                 125 ccc acc agc aat ggc tac tcg ggt tac aca ttc ggc gat gca agt tta     432
Pro Thr Ser Asn Gly Tyr Ser Gly Tyr Thr Phe Gly Asp Ala Ser Leu
    130                 135                 140 tat cat cct aaa tgc acc ata gat tac aat gat cag acg tct att gag     480
```

```
                Tyr His Pro Lys Cys Thr Ile Asp Tyr Asn Asp Gln Thr Ser Ile Glu
                145                 150                 155                 160 caa tgc tgg gtt gct gac gag ttg cct gat att gac act gaa aat tct         528
Gln Cys Trp Val Ala Asp Glu Leu Pro Asp Ile Asp Thr Glu Asn Ser
                    165                 170                 175 gac aac gtg gcc att ctc aac gac atc gtc tcc ggc tgg gtg ggt aac         576
Asp Asn Val Ala Ile Leu Asn Asp Ile Val Ser Gly Trp Val Gly Asn
                180                 185                 190 tat agc ttt gac ggc atc cgc att gat act gtc aag cat att cgc aag         624
Tyr Ser Phe Asp Gly Ile Arg Ile Asp Thr Val Lys His Ile Arg Lys
            195                 200                 205 gac ttt tgg aca ggc tac gca gaa gct gcc ggc gta ttc gca act gga         672
Asp Phe Trp Thr Gly Tyr Ala Glu Ala Ala Gly Val Phe Ala Thr Gly
        210                 215                 220 gag gtc ttc aat ggt gat ccg gcc tac gtt gga cct tat caa aag tac         720
Glu Val Phe Asn Gly Asp Pro Ala Tyr Val Gly Pro Tyr Gln Lys Tyr
225                 230                 235                 240 ctg cca tct ctc atc aat tac cca atg tat tac gct ttg aac gac gtc         768
Leu Pro Ser Leu Ile Asn Tyr Pro Met Tyr Tyr Ala Leu Asn Asp Val
                245                 250                 255 ttt gta tcc aaa agc aaa gga ttc agc cgc atc agc gaa atg cta gga         816
Phe Val Ser Lys Ser Lys Gly Phe Ser Arg Ile Ser Glu Met Leu Gly
            260                 265                 270 tca aat cgc aat gcg ttt gag gat acc agc gta ctt aca acg ttt gta         864
Ser Asn Arg Asn Ala Phe Glu Asp Thr Ser Val Leu Thr Thr Phe Val
        275                 280                 285 gac aac cat gac aat ccg cgc ttc ttg aac agt caa agc gac aag gct         912
Asp Asn His Asp Asn Pro Arg Phe Leu Asn Ser Gln Ser Asp Lys Ala
    290                 295                 300 ctc ttc aag aac gct ctc aca tac gta ctg cta ggt gaa ggc atc cca         960
Leu Phe Lys Asn Ala Leu Thr Tyr Val Leu Leu Gly Glu Gly Ile Pro
305                 310                 315                 320 att gtg tat tat ggt tct gag caa ggt ttc agc gga gga gcg gat cct        1008
Ile Val Tyr Tyr Gly Ser Glu Gln Gly Phe Ser Gly Gly Ala Asp Pro
                325                 330                 335 gct aac cgt gaa gtg ctg tgg acc acc aat tat gat aca tcc agc gat        1056
Ala Asn Arg Glu Val Leu Trp Thr Thr Asn Tyr Asp Thr Ser Ser Asp
            340                 345                 350 ctc tac caa ttt atc aag aca gtc aac agt gtc cgc atg aaa agc aac        1104
Leu Tyr Gln Phe Ile Lys Thr Val Asn Ser Val Arg Met Lys Ser Asn
        355                 360                 365 aag gcc gtc tac atg gat att tat gtt ggc gac aat gct tac gcc ttc        1152
Lys Ala Val Tyr Met Asp Ile Tyr Val Gly Asp Asn Ala Tyr Ala Phe
    370                 375                 380 aag cac ggc gat gct ttg gtt gtt ctc aat aac tat gga tca ggt tcc        1200
Lys His Gly Asp Ala Leu Val Val Leu Asn Asn Tyr Gly Ser Gly Ser
385                 390                 395                 400 aca aac caa gtc agc ttc agc gtt agt ggc aag ttc gat agc ggc gca        1248
Thr Asn Gln Val Ser Phe Ser Val Ser Gly Lys Phe Asp Ser Gly Ala
                405                 410                 415 agc ctc atg gat att gtc agt aac att acc acg gtg tcc tcg gat            1296
Ser Leu Met Asp Ile Val Ser Asn Ile Thr Thr Val Ser Ser Asp
            420                 425                 430 gga aca gtc act ttc aac ctt aaa gat gga ctt ccg gct atc ttc acc        1344
Gly Thr Val Thr Phe Asn Leu Lys Asp Gly Leu Pro Ala Ile Phe Thr
        435                 440                 445 tct gct                                                                1350
Ser Ala
    450
```

<210> SEQ ID NO 6
<211> LENGTH: 450
<212> TYPE: PRT
<213> ORGANISM: Rhizomucor pusillus

<400> SEQUENCE: 6

```
Ser Pro Leu Pro Gln Gln Arg Tyr Gly Lys Arg Ala Thr Ser Asp
1               5                   10                  15

Asp Trp Lys Gly Lys Ala Ile Tyr Gln Leu Leu Thr Asp Arg Phe Gly
            20                  25                  30

Arg Ala Asp Asp Ser Thr Ser Asn Cys Ser Asn Leu Ser Asn Tyr Cys
        35                  40                  45

Gly Gly Thr Tyr Glu Gly Ile Thr Lys His Leu Asp Tyr Ile Ser Gly
    50                  55                  60

Met Gly Phe Asp Ala Ile Trp Ile Ser Pro Ile Pro Lys Asn Ser Asp
65                  70                  75                  80

Gly Gly Tyr His Gly Tyr Trp Ala Thr Asp Phe Tyr Gln Leu Asn Ser
                85                  90                  95

Asn Phe Gly Asp Glu Ser Gln Leu Lys Ala Leu Ile Gln Ala Ala His
            100                 105                 110

Glu Arg Asp Met Tyr Val Met Leu Asp Val Val Ala Asn His Ala Gly
        115                 120                 125

Pro Thr Ser Asn Gly Tyr Ser Gly Tyr Thr Phe Gly Asp Ala Ser Leu
    130                 135                 140

Tyr His Pro Lys Cys Thr Ile Asp Tyr Asn Asp Gln Thr Ser Ile Glu
145                 150                 155                 160

Gln Cys Trp Val Ala Asp Glu Leu Pro Asp Ile Asp Thr Glu Asn Ser
                165                 170                 175

Asp Asn Val Ala Ile Leu Asn Asp Ile Val Ser Gly Trp Val Gly Asn
            180                 185                 190

Tyr Ser Phe Asp Gly Ile Arg Ile Asp Thr Val Lys His Ile Arg Lys
        195                 200                 205

Asp Phe Trp Thr Gly Tyr Ala Glu Ala Gly Val Phe Ala Thr Gly
    210                 215                 220

Glu Val Phe Asn Gly Asp Pro Ala Tyr Val Gly Pro Tyr Gln Lys Tyr
225                 230                 235                 240

Leu Pro Ser Leu Ile Asn Tyr Pro Met Tyr Tyr Ala Leu Asn Asp Val
                245                 250                 255

Phe Val Ser Lys Ser Lys Gly Phe Ser Arg Ile Ser Glu Met Leu Gly
            260                 265                 270

Ser Asn Arg Asn Ala Phe Glu Asp Thr Ser Val Leu Thr Thr Phe Val
        275                 280                 285

Asp Asn His Asp Asn Pro Arg Phe Leu Asn Ser Gln Ser Asp Lys Ala
    290                 295                 300

Leu Phe Lys Asn Ala Leu Thr Tyr Val Leu Leu Gly Glu Gly Ile Pro
305                 310                 315                 320

Ile Val Tyr Tyr Gly Ser Glu Gln Gly Phe Ser Gly Gly Ala Asp Pro
                325                 330                 335

Ala Asn Arg Glu Val Leu Trp Thr Thr Asn Tyr Asp Thr Ser Ser Asp
            340                 345                 350

Leu Tyr Gln Phe Ile Lys Thr Val Asn Ser Val Arg Met Lys Ser Asn
        355                 360                 365

Lys Ala Val Tyr Met Asp Ile Tyr Val Gly Asp Asn Ala Tyr Ala Phe
    370                 375                 380
```

```
Lys His Gly Asp Ala Leu Val Val Leu Asn Asn Tyr Gly Ser Gly Ser
385                 390                 395                 400

Thr Asn Gln Val Ser Phe Ser Val Ser Gly Lys Phe Asp Ser Gly Ala
            405                 410                 415

Ser Leu Met Asp Ile Val Ser Asn Ile Thr Thr Val Ser Ser Asp
        420                 425                 430

Gly Thr Val Thr Phe Asn Leu Lys Asp Gly Leu Pro Ala Ile Phe Thr
            435                 440                 445

Ser Ala
    450

<210> SEQ ID NO 7
<211> LENGTH: 111
<212> TYPE: DNA
<213> ORGANISM: Aspergillus niger
<220> FEATURE:
<221> NAME/KEY: CDS
<222> LOCATION: (1)..(111)
<223> OTHER INFORMATION: Linker

<400> SEQUENCE: 7 act ggc ggc acc act acg acg gct acc ccc act gga tcc ggc agc gtg        48
Thr Gly Gly Thr Thr Thr Thr Ala Thr Pro Thr Gly Ser Gly Ser Val
1               5                   10                  15 acc tcg acc agc aag acc acc gcg act gct agc aag acc agc acc agt        96
Thr Ser Thr Ser Lys Thr Thr Ala Thr Ala Ser Lys Thr Ser Thr Ser
            20                  25                  30 acg tca tca acc tcc                                                   111
Thr Ser Ser Thr Ser
        35

<210> SEQ ID NO 8
<211> LENGTH: 37
<212> TYPE: PRT
<213> ORGANISM: Aspergillus niger

<400> SEQUENCE: 8

Thr Gly Gly Thr Thr Thr Thr Ala Thr Pro Thr Gly Ser Gly Ser Val
1               5                   10                  15

Thr Ser Thr Ser Lys Thr Thr Ala Thr Ala Ser Lys Thr Ser Thr Ser
            20                  25                  30

Thr Ser Ser Thr Ser
        35

<210> SEQ ID NO 9
<211> LENGTH: 324
<212> TYPE: DNA
<213> ORGANISM: Aspergillus niger
<220> FEATURE:
<221> NAME/KEY: CDS
<222> LOCATION: (1)..(324)
<223> OTHER INFORMATION: CBM

<400> SEQUENCE: 9 tgt acc act ccc acc gcc gtg gct gtg act ttc gat ctg aca gct acc        48
Cys Thr Thr Pro Thr Ala Val Ala Val Thr Phe Asp Leu Thr Ala Thr
1               5                   10                  15 acc acc tac ggc gag aac atc tac ctg gtc gga tcg atc tct cag ctg        96
Thr Thr Tyr Gly Glu Asn Ile Tyr Leu Val Gly Ser Ile Ser Gln Leu
            20                  25                  30 ggt gac tgg gaa acc agc gac ggc ata gct ctg agt gct gac aag tac      144
Gly Asp Trp Glu Thr Ser Asp Gly Ile Ala Leu Ser Ala Asp Lys Tyr
```

```
                  35                  40                  45
act tcc agc gac ccg ctc tgg tat gtc act gtg act ctg ccg gct ggt        192
Thr Ser Ser Asp Pro Leu Trp Tyr Val Thr Val Thr Leu Pro Ala Gly
         50                  55                  60 gag tcg ttt gag tac aag ttt atc cgc att gag agc gat gac tcc gtg        240
Glu Ser Phe Glu Tyr Lys Phe Ile Arg Ile Glu Ser Asp Asp Ser Val
 65                  70                  75                  80 gag tgg gag agt gat ccc aac cga gaa tac acc gtt cct cag gcg tgc        288
Glu Trp Glu Ser Asp Pro Asn Arg Glu Tyr Thr Val Pro Gln Ala Cys
                 85                  90                  95 gga acg tcg acc gcg acg gtg act gac acc tgg cgg                        324
Gly Thr Ser Thr Ala Thr Val Thr Asp Thr Trp Arg
            100                 105

<210> SEQ ID NO 10
<211> LENGTH: 108
<212> TYPE: PRT
<213> ORGANISM: Aspergillus niger

<400> SEQUENCE: 10

Cys Thr Thr Pro Thr Ala Val Ala Val Thr Phe Asp Leu Thr Ala Thr
  1               5                  10                  15

Thr Thr Tyr Gly Glu Asn Ile Tyr Leu Val Gly Ser Ile Ser Gln Leu
             20                  25                  30

Gly Asp Trp Glu Thr Ser Asp Gly Ile Ala Leu Ser Ala Asp Lys Tyr
         35                  40                  45

Thr Ser Ser Asp Pro Leu Trp Tyr Val Thr Val Thr Leu Pro Ala Gly
     50                  55                  60

Glu Ser Phe Glu Tyr Lys Phe Ile Arg Ile Glu Ser Asp Asp Ser Val
 65                  70                  75                  80

Glu Trp Glu Ser Asp Pro Asn Arg Glu Tyr Thr Val Pro Gln Ala Cys
                 85                  90                  95

Gly Thr Ser Thr Ala Thr Val Thr Asp Thr Trp Arg
            100                 105

<210> SEQ ID NO 11
<211> LENGTH: 34
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(34)
<223> OTHER INFORMATION: Primer EuAMF1

<400> SEQUENCE: 11
acgtacggat ccaytwctay wcbtggachc gyga                                   34

<210> SEQ ID NO 12
<211> LENGTH: 30
<212> TYPE: DNA
<213> ORGANISM: Artificial sequence
<220> FEATURE:
<223> OTHER INFORMATION: Synthetic construct

<400> SEQUENCE: 12
gtacgtaagc ttrtcytcrg ggtavcgdcc                                        30

<210> SEQ ID NO 13
<211> LENGTH: 24
<212> TYPE: DNA
```

<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(34)
<223> OTHER INFORMATION: Primer 50311F1

<400> SEQUENCE: 13
cgattcacac ctgggacatc aagg                                              24

<210> SEQ ID NO 14
<211> LENGTH: 24
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(24)
<223> OTHER INFORMATION: Primer 50311R2

<400> SEQUENCE: 14
aagacacagt accagacggg ttgg                                              24

<210> SEQ ID NO 15
<211> LENGTH: 24
<212> TYPE: DNA
<213> ORGANISM: Artificial sequence
<220> FEATURE:
<223> OTHER INFORMATION: Synthetic construct

<400> SEQUENCE: 15
ggtggcagca ccgtcgctgt aacc                                              24

<210> SEQ ID NO 16
<211> LENGTH: 34
<212> TYPE: DNA
<213> ORGANISM: Artificial sequence
<220> FEATURE:
<223> OTHER INFORMATION: Synthetic construct

<400> SEQUENCE: 16
cagcacggat ccaagatgcg tctcccacaa cttg                                   34

<210> SEQ ID NO 17
<211> LENGTH: 37
<212> TYPE: DNA
<213> ORGANISM: Artificial sequence
<220> FEATURE:
<223> OTHER INFORMATION: Synthetic construct

<400> SEQUENCE: 17
gcatcaaggc ggccgcctag cgccaggaat cgttggc                                37

<210> SEQ ID NO 18
<211> LENGTH: 35
<212> TYPE: DNA
<213> ORGANISM: Artificial sequence
<220> FEATURE:
<223> OTHER INFORMATION: Synthetic construct

<400> SEQUENCE: 18
gcggatccac catgcgtctc ccacaacttg gagtc                                  35

<210> SEQ ID NO 19
<211> LENGTH: 32

-continued

```
<212> TYPE: DNA
<213> ORGANISM: Artificial sequence
<220> FEATURE:
<223> OTHER INFORMATION: Synthetic construct

<400> SEQUENCE: 19
agcttgatta cgggccagag cgtgttcgtg ac                                  32

<210> SEQ ID NO 20
<211> LENGTH: 30
<212> TYPE: DNA
<213> ORGANISM: Artificial sequence
<220> FEATURE:
<223> OTHER INFORMATION: Synthetic construct

<400> SEQUENCE: 20
cgaacacgct ctggcccgta atcaagcttg                                     30

<210> SEQ ID NO 21
<211> LENGTH: 34
<212> TYPE: DNA
<213> ORGANISM: Artificial sequence
<220> FEATURE:
<223> OTHER INFORMATION: Synthetic construct

<400> SEQUENCE: 21
gggcggccgc tagcgccagg aatcgttggc agta                                34
```

POLYPEPTIDES HAVING GLUCOAMYLASE ACTIVITY AND POLYNUCLEOTIDES ENCODING SAME

CROSS-REFERENCE TO RELATED APPLICATIONS

This application is a 35 U.S.C. 371 national application of PCT/US2007/066618 filed Apr. 13, 2007, which claims priority or the benefit under 35 U.S.C. 119 of U.S. provisional application No. 60/793,128 filed Apr. 19, 2006, the contents of which are fully incorporated herein by reference.

CROSS-REFERENCE TO A SEQUENCE LISTING

This application contains a Sequence Listing in computer readable form. The computer readable form is incorporated herein by reference.

FIELD OF THE INVENTION

The present invention relates to polypeptides having glucoamylase activity and polynucleotides encoding the polypeptides. The invention also relates to nucleic acid constructs, vectors, and host cells comprising the polynucleotides as well as methods for producing and using the polypeptides, and to the use of glucoamylases of the invention for starch conversion to producing fermentation products, such as ethanol, and syrups, such as glucose. The invention also relates to a composition comprising a glucoamylase of the invention.

BACKGROUND OF THE INVENTION

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starchy material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic add, gluconate, lactic add, succinic acid, 2,5-diketo-D-gluconic acid); ketones (e.g., acetone); amino acids (e.g., glutamic acid), gases (e.g., $H_2$ and $CO_2$), and more complex compounds, including, for example, antibiotics (e.g., penicillin and tetracycline); enzymes: vitamins (e.g., riboflavin, $B_{12}$, beta-carotene), hormones, and other compounds which are difficult to produce synthetically. Fermentation processes are also commonly used in the consumable alcohol (e.g., beer and wine), dairy (e.g., in the production of yoghurt and cheese), leather, and tobacco industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

Boel et al. (1984), EMBO J. 3 (5), p. 1097-1102 disclose *Aspergillus niger* G1 or G2 glucoamylase.

U.S. Pat. No. 4,727,046 discloses a glucoamylase derived from *Corticium rolfsii* which is also referred to as *Athelia rolfsii*.

WO 84/02921 discloses a glucoamylase derived from *Aspergillus awamori*.

WO 99/28248 discloses a glucoamylase derived from *Talaromyces emersonii*.

WO 00/75296 discloses a glucoamylase derived from *Thermoascus crustaceus*.

WO 2006/069289 discloses glucoamylases derived from *Trametes cingulate, Pachykytospora papyracea*, and *Leucopaxillus giganteus*.

It is an object of the present invention to provide polypeptides having glucoamylase activity and polynucleotides encoding the polypeptides and which provide a high yield in fermentation product production processes, such as ethanol production processes, including one-step ethanol fermentation processes from un-gelatinized raw (or uncooked) starch.

SUMMARY OF THE INVENTION

The present invention relates to polypeptides having glucoamylase activity selected from the group consisting of:
(a) a polypeptide having an amino acid sequence which has at least 60% identity with amino acids for mature polypeptide amino acids 1 to 558 of SEQ ID NO: 2;
(b) a polypeptide which is encoded by a nucleotide sequence (i) which hybridizes under at least low stringency conditions with nucleotides 61 to 2301 of SEQ ID NO: 1, or (ii) which hybridizes under at least low stringency conditions with the cDNA sequence contained in nucleotides 61 to 1734 of SEQ ID NO: 3, or (iii) a complementary strand of (i) or (ii);
(c) a variant comprising a conservative substitution, deletion, and/or insertion of one or more amino acids of amino acids 1 to 558 of SEQ ID NO: 2.

The present invention also relates to polynucleotides encoding polypeptides having glucoamylase activity, selected from the group consisting of:
(a) a polynucleotide encoding a polypeptide having an amino acid sequence which has at least 60% identity with the mature polypeptide amino acids 1 to 558 of SEQ ID NO: 2;
(b) a polynucleotide having at least 60% identity with nucleotides 61 to 2301 of SEQ ID NO: 1; or
(c) a polynucleotide having at least 60% identity with nucleotides 61 to 1734 of SEQ ID NO: 3;
(d) a polypeptide which is encoded by a nucleotide sequence (i) which hybridizes under at least low stringency conditions with nucleotides 61 to 2301 of SEQ ID NO: 1, or (ii) which hybridizes under at least low stringency conditions with the cDNA sequence contained in nucleotides 61 to 1734 of SEQ ID NO: 3, or (iii) a complementary strand of (i) or (ii).

In a preferred embodiment the polypeptide is derivable from a strain of the genus *Peniphora*, preferably a strain of the species *Peniphora rufomarginata* or *E. coli* strain deposited at DSMZ on 3 Apr. 2006 under the terms of the Budapest Treaty on the International Recognition of the Deposit of Microorganisms for the Purposes of Patent Procedure at Deutshe Sammmlung von Microorganismen and Zeilkulturen GmbH (DSMZ), Mascheroder Weg 1b, D-38124 Braunschweig DE. The clone was given the no. DSM 18150. Deposited strain DSM 18150 harbors plasmid pENI2516 comprising a sequence that, to the best belief of the inventors, is identical to SEQ ID NO: 1. A specific polypeptide of the invention is the mature polypeptide obtained when expressing plasmid pENI2516 in a suitable fungal host cell.

The present invention also relates to methods for producing such polypeptides having glucoamylase activity comprising (a) cultivating a recombinant host cell comprising a nucleic acid construct comprising a polynucleotide encoding the polypeptide under conditions conducive for production of the polypeptide, and (b) recovering the polypeptide.

The present invention also relates to processes of producing fermentation products or syrups.

DEFINITIONS

Glucoamylase activity: The term glucoamylase (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the "Materials & Methods"-section below.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the glucoamylase activity of the polypeptide consisting of the amino acid sequence shown as amino acids 1 to 558 of SEQ ID NO: 2.

Polypeptide: The term "polypeptide" as used herein refers to an isolated polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form".

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide Fragment: The term "polypeptide fragment" is defined herein as a polypeptide having one or more amino acids deleted from the amino and/or carboxyl terminus of SEQ ID NO: 2, or homologous sequences thereof, wherein the fragment has glucoamylase activity.

Subsequence: The term "subsequence" is defined herein as a nucleotide sequence having one or more nucleotides deleted from the 5 and/or 3' end of SEQ ID NO: 1 or 3, or homologous sequences thereof, wherein the subsequence encodes a polypeptide fragment having glucoamylase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e. that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semi-synthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, pro-peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptide consisting of the amino acids 1 to 558 of SEQ ID NO: 2, as well as genetic manipulation of the DNA encoding the polypeptides. The modification(s) can be substitution(s), deletion(s) and/or insertions(s) of the amino acid(s) as well as replacement(s) of amino acid side chain(s).

Artificial variant: When used herein, the term "artificial variant" means a polypeptide having glucoamylase activity produced by an organism expressing a modified nucleotide sequence of SEQ ID NOS: 1 (genomic DNA) or 3 (cDNA). The modified nucleotide sequence is obtained through human intervention by modification of the nucleotide sequence disclosed in SEQ ID NO: 1 or 3.

DETAILED DESCRIPTION OF THE INVENTION

Polypeptides Having Glucoamylase Activity

In a first aspect, the present invention relates to polypeptides having an amino acid sequence which has a degree of identity to amino acids 1 to 558 of SEQ ID NO: 2 (i.e. mature polypeptide).

In an embodiment the polypeptide is a variant comprising a conservative substitution, deletion, and/or insertion of one or more amino acids of amino acids 1 to 558 of SEQ ID NO: 2.

In an embodiment the amino acid sequence has glucoamylase activity and is at least 60%, preferably at least 70%, preferably at least 80%, more preferably at least 85%, even more preferably at least 90%, most preferably at least 95%, more preferred at least 96%, even more preferred at least 97%, even more preferred at least 98%, even more preferably at least 99% identical to the mature part of SEQ ID NO: 2 (hereinafter "homologous polypeptides").

In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 1 to 558 of SEQ ID NO: 2.

A polypeptide of the present invention preferably comprises the mature amino acid sequences of SEQ ID NO: 2, or allelic variants thereof; or fragments thereof that have glucoamylase activity, e.g., the catalytic domain.

Catalytic Domain

In an aspect, the invention relates to polypeptides that comprise the catalytic region/domain of the amino acid sequences of SEQ ID NO: 2.

The catalytic region/domain of the invention exhibiting glucoamylase activity, preferably derived from a strain of *Peniophora*, especially a strain of preferably *Peniophora ruromarginata*, is located from amino acids 1 to 448 in SEQ ID NO: 2. In one embodiment the region may be considered to include the linker region from amino acids 449 to 463 of SEQ ID NO: 2, or part thereof. The putative binding domain is encoded by polynucleotides 1845 to 2301 in SEQ ID NO: 1 or polynucleotides 1450-1734 of SEQ ID NO: 3.

In a preferred embodiment the invention relates to a catalytic region which has at least 60% identity, preferably at least 65% identity, more preferably at least 70% identity, more preferably at least 75% identity, more preferably at least 80% identity, more preferably at least 85% identity, even more preferably at least 90% identity, most preferably at least 95% identity, more preferred at least 96% identity, even more preferred at least 97% identity, even more preferred at least 98% identity, even more preferably at least 99% identity, especially 100% identity to amino acids 1 to 448 in SEQ ID NO: 2, and which have glucoamylase activity (hereinafter "homologous polypeptides"). In a preferred aspect, the homologous catalytic regions have amino acid sequences which differs by ten amino acids, preferably by five amino acids, more preferably by four amino acids, even more preferably by three amino acids, most preferably by two amino acids, and even most preferably by one amino acid from amino acids 1 to 448 of SEQ ID NO: 2.

Binding Domain

In another aspect, the invention relates to polypeptides having carbohydrate-binding affinity, preferably starch-binding affinity.

The binding domain in *Peniophora ruformarginata* glucoamylase is located from amino acid 464 to 558 of SEQ ID NO: 2 and is encoded by polynucleotides 1845-2301 in SEQ ID NO: 1 or 1450-1734 of SEQ ID NO: 3.

Consequently, in this aspect the invention relates to a polypeptide having carbohydrate-binding affinity, selected from the group consisting of:
(a) i) a polypeptide comprising an amino acid sequence which has at least 60% identity with amino acids 464 to 558 of SEQ ID NO: 2;
(b) a polypeptide which is encoded by a nucleotide sequence which hybridizes under low stringency conditions with a polynucleotide probe which has the complementary strand of nucleotides 1845 to 2301 of SEQ ID NO: 1 or nucleotides 1450 to 1734 of SEQ ID NO: 3, respectively;
(c) a fragment of (a) or (b) that has carbohydrate binding affinity.

In a preferred embodiment the carbohydrate binding affinity is starch-binding affinity.

In a preferred embodiment the invention relates to a polypeptide having carbohydrate binding affinity which has at least 60% identity, preferably at least 70% identity, more preferably at least 75% identity, more preferably at least 80% identity, more preferably at least 85% identity, even more preferably at least 90% identity, most preferably at least 95% identity, more preferred at least 96% identity, even more preferred at least 97% identity, even more preferred at least 98% identity, even more preferably at least 99% identity, especially 100% identity to amino acids 464 to 558 in SEQ ID NO: 2.

In a preferred aspect, homologous binding domains have amino acid sequences which differ by ten amino acids, preferably by five amino acids, more preferably by four amino acids, even more preferably by three amino acids, most preferably by two amino acids, and even most preferably by one amino acid from amino acids 464 to 558 of SEQ ID NO: 2.

The invention also relates to a polypeptide having carbohydrate-binding affinity, where the polypeptide is an artificial variant which comprises an amino acid sequence that has at least one substitution, deletion and/or insertion of an amino acid as compared to amino acids 464 to 558 of SEQ ID NO: 2.

The invention also relates to a polypeptide having carbohydrate-binding affinity, where the polypeptide is an artificial variant which comprises an amino acid sequence that has at least one substitution, deletion and/or insertion of an amino acid as compared to the amino acid sequence encoded by the carbohydrate-binding domain encoding part of the polynucleotide sequences shown in position 1845-2301 in SEQ ID NO: 1, or 1450 to 1734 in SEQ ID NO: 3.

Hybrids

The glucoamylases or catalytic regions of the invention may be linked, via a linker sequence or directly, to one or more foreign binding domains (also referred to as binding modules (CBM)). A "foreign" binding domain is a binding-domain that is not derived from the wild-type glucoamylase of the invention. The binding-domain is preferably a carbohydrate-binding domain (i.e., having affinity for binding to a carbohydrate), especially a starch-binding domain or a cellulose-binding domain. Preferred binding domains are of fungal or bacterial origin. Examples of specifically contemplated starch-binding domains are disclosed in WO 2005/003311 which is hereby incorporated by reference.

In a preferred embodiment the linker in a glucoamylase of the invention is replaced with a more stable linker, i.e., a linker that is more difficult to cut than the parent linker. This is done to avoid that the binding-domain is cleaved off. Specifically contemplated stable linkers include the *Aspergillus kawachii* linker:

TTTTTTAAAT STSKATTSSSSSSAAATTSSS (SEQ ID NO: 4)

Thus, in a preferred embodiment the invention relates to a hybrid glucoamylase having the amino acid sequence shown in SEQ ID NO: 2, wherein the native linker located from amino acids 449 to 463 of SEQ ID NO: 2, or part thereof, is replaced with the *Aspergillus kawachii* linker shown in SEQ ID NO: 4.

Thus, the invention also relates to hybrids consisting of a glucoamylase of the invention or catalytic domain of the invention having glucoamylase activity fused to a stable linker (e.g., *Aspergillus kawachii* linker) and one or more carbohydrate-binding domains, e.g., a carbohydrate-binding module (CBM) disclosed in WO 2005/003311 on page 5, line 30 to page 8, line 12, hereby incorporated by reference.

Hybridization

In another aspect, the present invention relates to polypeptides having glucoamylase activity which are encoded by polynucleotides (i) which hybridizes under at least low stringency conditions, preferably medium stringency conditions, more preferably medium-high stringency conditions, even more preferably high stringency conditions, and most preferably very high stringency conditions with a nucleotide sequence with nucleotides 61 to 2301 of SEQ ID NO: 1 (*Peniophora* genomic DNA) or nucleotides 61 to 1734 of SEQ ID NO: 3 (*Peniophora* cDNA), or (ii) a subsequence of (i), or (iii) a complementary strand of (i) or (ii) (J. Sambrook, E. F. Fritsch, and T. Maniatis, 1989, *Molecular Cloning, A Laboratory Manual,* 2d edition, Cold Spring Harbor, N.Y.). A subsequence of SEQ ID NOS: 1 or 3 contains at least 100 contiguous nucleotides or preferably at least 200 continguous nucleotides. Moreover, the subsequence may encode a polypeptide fragment which has glucoamylase activity.

The nucleotide sequence of SEQ ID NOS: 1 or 3, or a subsequence thereof, as well as the amino acid sequence of SEQ ID NO: 2, or a fragment thereof, may be used to design a nucleic acid probe to identify and clone DNA encoding polypeptides having glucoamylase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{3}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having glucoamylase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NOS: 1 or 3, or a subsequence thereof, the carrier material is used in a Southern blot.

For purposes of the present invention, hybridization indicates that the nucleotide sequences hybridize to labeled nucleic acid probes corresponding to the nucleotide sequence shown in SEQ ID NOS: 1 or 3, its complementary strands, or subsequences thereof, under low to very high stringency conditions, Molecules to which the nucleic acid probe hybridizes under these conditions can be detected using X-ray film.

In a preferred embodiment, the nucleic acid probe is nucleotides 61 to 2301 of SEQ ID NO: 1 or nucleotides 61 to 1734 of SEQ ID NO: 3. In another preferred aspect, the nucleic acid probe is a polynucleotide sequence which encodes the catalytic region between amino acids 1-448 of SEQ ID NO: 2.

In another aspect the invention relates to nucleic acid probes that encode the binding domain in amino acids 464 to 558 of SEQ ID NO: 2.

In another preferred aspect, the nucleic acid probe is the mature polypeptide coding region of SEQ ID NOS: 1 or 3, respectively.

In another preferred aspect, the nucleic acid probe is the part of the sequences in plasmid pENI2516 coding for the mature polypeptides of the invention. Plasmid pENI2516 which are contained in *Escherichia coli* DSM 18150 encode polypeptides having glucoamylase activity.

For long probes of at least 100 nucleotides in length, low to very high stringency conditions are defined as prehybridization and hybridization at 42° C. in 5×SSPE, 0.3% SDS, 200 micro g/ml sheared and denatured salmon sperm DNA, and either 25% formamide for low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Under salt-containing hybridization conditions, the effective $T_m$ is what controls the degree of identity required between the probe and the filter bound DNA for successful hybridization. The effective $T_m$ may be determined using the formula below to determine the degree of identity required for two DNAs to hybridize under various stringency conditions.

$$\text{Effective } T_m = 81.5 + 16.6(\log M[\text{Na}^+]) + 0.41(\% G+C) - 0.72(\% \text{ formamide})$$

(See www.ndsu.nodak.edu/insruct/mcclean/plsc731/dna/dna6.htm)

Variants

In a further aspect, the present invention relates to artificial variants comprising a conservative substitution, deletion, and/or insertion of one or more amino acids in SEQ ID NO: 2, or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline, Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., glucoamylase activity) to identify amino acid residues that are critical to the activity of the molecule. See also, Hilton et al. 1996, *J. Biol. Chem.* 271: 4699-4708. The active site of the enzymes or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312, Smith et al., 1992, *J. Mol. Biol.* 224: 899-904; Wlodaver et al., 1992, *FEBS Lett.* 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57: Bowie and Sauer, 1989, *Proc. Natl. Acad. Sci. USA* 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al. 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids in position 1 to 558 of SEQ ID NO: 2, is 10, preferably 9, more preferably 8, more preferably 7, more preferably at most 6, more preferably at most 5, more preferably 4, even more preferably 3, most preferably 2, and even most preferably 1.

Sources of Polypeptides Having Glucoamylase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

In a preferred embodiment, the glucoamylase of the invention derived from the class Basidiomycetes. In a more preferred embodiment a glucoamylase of the invention is derived from a strain of the genus *Peniophora*, more preferably from a strain of the species *Peniophora reformarginata*, or deposited as *Escherichia coli* clone DSM 18150.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

The *Peniophora refomarginata* strain was collected in Denmark in 1997.

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention. In a preferred aspect, the nucleotide sequence is set forth in any of SEQ ID NO: 1 (genomic DNA) or 3 (cDNA), respectively. In another more preferred aspect, the nucleotide sequence is the sequence contained in plasmid pENI2516 that is contained in *Escherichia coli* DSM 18150 In another preferred aspect, the nucleotide sequence is the mature polypeptide coding region of any of SEQ ID NOS: 1 or 3, respectively. The present invention also encompasses nucleotide sequences which encode a polypeptide having the amino acid sequence of SEQ ID NO: 2, or the mature polypeptide thereof, which differs from SEQ ID NOS: 1 or 3, respectively, by virtue of the degeneracy of the genetic code. The present invention also relates to subsequences of any of SEQ ID NOS: 1 or 3, respectively, which encode fragments of SEQ ID NO: 2 that have glucoamylase activity.

The present invention also relates to mutant polynucleotides comprising at least one mutation in the mature polypeptide coding sequence of any of SEQ ID NOS: 1 or 3, respectively, in which the mutant nucleotide sequence encodes a polypeptide which consists of amino acids 1 to 558 of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from any organism, especially a strain of the genus *Peniophora* or other or related organisms and thus, for example, may be an allelic or species variant of the polypeptide encoding region of the nucleotide sequences.

The present invention also relates to polynucleotides having nucleotide sequences which have a degree of identity to the mature polypeptide coding sequence of SEQ ID NO: 1 (i.e. nucleotides 61 to 2301), or SEQ ID NO: 3 (i.e., nucleotides 61 to 1734), respectively, of at least 60%, preferably at least 65%, more preferably at least 70%, more preferably at least 75%, more preferably at least 80%, more preferably at least 85%, more preferably at least 90%, even more preferably at least 95%, even more prefer ably 96%, even more 97%, even more 98%, and most preferably at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide encoding region of any of SEQ ID NOS: 1 or 3, respectively, e.g. subsequences thereof, and/or by introduction of nucleotide substitutions, which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for glucoamylase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al. 1992, FEBS Letters 309: 59-64).

The present invention also relates to isolated polynucleotides encoding a polypeptide of the present invention, (i) which hybridize under low stringency conditions, more preferably medium stringency conditions, more preferably medium-high stringency conditions, even more preferably high stringency conditions, and most preferably very high stringency conditions with nucleotides 61 to 2301 of SEQ ID NO: 1 or nucleotides 61 to 1734 of SEQ ID NO: 3, respectively, or (ii) a complementary strand of (i); or allelic variants and subsequences thereof (Sambrook et al. 1989, supra), as defined herein.

The present invention also relates to isolated polynucleotides obtained by (a) hybridizing a population of DNA under low, medium, medium-high, high, or very high stringency conditions with (i) nucleotides 61 to 2301 of SEQ ID NO: 1 or nucleotides 61 to 1734 of SEQ ID NO: 3, respectively, or (ii) a complementary strand of (i); and (b) Isolating the hybridizing polynucleotide, which encodes a polypeptide having glucoamylase activity, Nucleic Acid Constructs The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase. *Aspergillus nidulans* acetamidase, *Fusarium venenatum* glucoamylase (WO 00/56900), *Fusarium venenatum* Daria (WO 00/56900). *Fusarium venenatum* Quinn (WO 00/56900), *Fusarium oxysporum* trypsin-like protease (WO 96/00787), *Trichoderma reesei* beta-glucosidase *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1). *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3 terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase, Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a eukaryote, such as a mammalian, insect, plant, or fungal cell.

In a preferred aspect, the host cell is a fungal cell. "Fungi" as used herein includes the phyla *Ascomycota, Basidiomycota, Chytridiomycota*, and *Zygomycota* (as defined by Hawksworth et al., in, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes) Since the classification of yeast may change in the future, for the purposes of this invention, yeast shall be defined as described in Biology and Activities of Yeast (Skinner, F. A. Passmore, S. M., and Davenport, R. R., eds, *Soc. App. Bacteria Symposium Series* No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipotytica* cell.

In another more preferred aspect, the fungal host cell is a filamentous fungal cell. "Filamentous fungi" include all filamentous forms of the subdivision *Eumycota* and *Oomycota* (as defined by Hawksworth at, 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger, Aspergillus kawachii*, or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioictes*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa*, or *Ceriporiopsis subvermispora, Coprinus cinereus, Coriolus hirsutus, Humicola isolens, Humicola lanuginosa, Mucor miehei, Myceliophthora thermophila, Neurospora crease, Penicillium purpurogenum, Phanerochaete chrysosporium, Phlebia radiate, Pleurotus eryngii, Thielavia terrestris, Trametes villosa, Trametes versicolor, Trichoderma harzianum, Trichoderma koningii, Trichoderma longibrachiatum, Trichoderma ressei*, or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York: Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is a strain of the genus *Peniophora*, more preferably a strain of the species *Peniophora rufomarginata*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a nucleotide sequence having the mature polypeptide coding region of SEQ ID NOS: 1 or 3, respectively, wherein the nucleotide sequence encodes a polypeptide which consists of amino acids 1 to 558 of SEQ ID NO: 2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having glucoamylase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an anti-nutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al, 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev, Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Viola faba* promoter from the legumin B4 and the unknown seed protein gene from *Viola faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mita and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g. ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a polynucleotide encoding a polypeptide having glucoamylase activity of the present invention under conditions conducive for production of the polypeptide; and (b) recovering the polypeptide.

Compositions

The present invention also relates to compositions comprising a polypeptide of the present invention. Preferably, the compositions are enriched in such a polypeptide. The term "enriched" indicates that the glucoamylase activity of the composition has been increased, e.g., by an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*, *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Combination of Glucoamylase and Acid Alpha-amylase

According to this aspect of the invention a glucoamylase of the invention may be combined with an alpha-amylase, preferably acid alpha-amylase in a ratio of between 0.3 and 5.0 AFAU/AGU. More preferably the ratio between acid alpha-amylase activity and glucoamylase activity is at least 0.35, at least 0.40, at least 050, at least 0.60, at least 0.7, at least 0.8, at least 0.9, at least 1.0, at least 1.1, at least 1.2, at least 1.3, at least 1.4, at least 1.5, at least 1.6, at least 1.7, at least 1.8, at least 1.85, or even at least 1.9 AFAU/AGU. However, the ratio between acid alpha-amylase activity and glucoamylase activity should preferably be less than 4.5, less than 4.0, less than 3.5, less than 3.0, less than 25, or even less than 2.25 AFAU/AGU. In AUU/AGI the activities of acid alpha-amylase and glucoamylase are preferably present in a ratio of between 0.4 and 6.5 AUU/AGI. More preferably the ratio between acid alpha-amylase activity and glucoamylase activity is at least 0.45, at least 0.50, at least 0.60, at least 0.7, at least 08, at least 0.9, at least 1.0, at least 1.1, at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4, or even at least 2.5 AUU/AGI, However, the ratio between acid alpha-amylase activity and glucoamylase activity is preferably less than 6.0, less than 55, less than 4.5, less than 4.0, less than 3.5, or even less than 3.0 AUU/AGI.

Above composition is suitable for use in a starch conversion process mentioned below for producing syrup and fermentation products, such as ethanol.

Examples are given below of preferred uses of the polypeptide compositions of the invention. The dosage of the polypeptide composition of the invention and other conditions under which the composition is used may be determined on the basis of methods known in the art.

Uses

The present invention is also directed to processes/methods for using the polypeptides having glucoamylase activity of the invention.

Uses according to the invention include starch conversion of starch to e.g., syrup and fermentation products, including ethanol and beverages. Examples of processes where a glucoamylase of the invention may be used include the ones described in: WO 2004/081193, WO 2004/080923, WO 2003/66816, WO 2003/66826, and WO 92/20777 which are hereby all incorporated by reference.

Production of Fermentation Products

Processes for Producing Fermentation Products from Gelatinized Starch-containing Material In this aspect the present invention relates to a process for producing a fermentation product, especially ethanol, from starch-containing material, which process includes a liquefaction step and sequentially or simultaneously performed saccharification and fermentation steps.

The invention relates to a process for producing a fermentation product from starch-containing material comprising the steps of:

(a) liquefying starch-containing material;
(b) saccharifying the liquefied material obtained in step (a) using a glucoamylase of the invention;
(c) fermenting the saccharified material using a fermenting organism.

The fermentation product, such as especially ethanol, may optionally be recovered after fermentation, e.g., by distillation. Suitable starch-containing starting materials are listed in the section "Starch-containing materials"-section below. Contemplated enzymes are listed in the "Enzymes"-section below. The liquefaction is preferably carried out in the presence of an alpha-amylase. The fermentation is preferably carried out in the presence of yeast, preferably a strain of *Saccharomyces*. Suitable fermenting organisms are listed in the "Fermenting Organisms"-section below. In preferred embodiments step (b) and (c) are carried out sequentially or simultaneously (i.e., as SSF process).

In a particular embodiment, the process of the invention further comprises, prior to the step (a), the steps of:

x) reducing the particle size of the starch-containing material, preferably by milling:
y) forming a slurry comprising the starch-containing material and water.

The aqueous slurry may contain from 10-40 wt-%, preferably 25-35 wt-% starch-containing material. The slurry is heated to above the gelatinization temperature and alpha-amylase, preferably bacterial and/or acid fungal alpha-amylase, may be added to initiate liquefaction (thinning). The slurry may in an embodiment be jet-cooked to further gelatinize the slurry before being subjected to an alpha-amylase in step (a) of the invention.

More specifically liquefaction may be carried out as a three-step hot slurry process. The slurry is heated to between 60-95° C., preferably 80-85° C., and alpha-amylase is added to initiate liquefaction (thinning). Then the slurry may be jet-cooked at a temperature between 95-140° C., preferably 105-125° C. for 1-15 minutes, preferably for 3-10 minute, especially around 5 minutes. The slurry is cooled to 60-95° C. and more alpha-amylase is added to finalize hydrolysis (secondary liquefaction). The liquefaction process is usually carried out at pH 4.5-6.5, in particular at a pH between 5 and 6. Milled and liquefied whole grains are known as mash.

The saccharification in step (b) may be carried out using conditions well know in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 30-65° C., typically around 60° C., and at a pH between 4 and 5, normally at about pH 4.5.

The most widely used process in fermentation product, especially ethanol, production is the simultaneous saccharification and fermentation (SSF) process, in which there is no holding stage for the saccharification, meaning that fermenting organism, such as yeast, and enzyme(s) may be added together. SSF may typically be carried out at a temperature between 25° C. and 40° C., such as between 29° C. and 35° C., such as between 30° C. and 34° C., such as around 32° C. According to the invention the temperature may be adjusted up or down during fermentation.

In accordance with the present invention the fermentation step (c) includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g. $H_2$ and $CO_2$); antibiotics (e.g., penicillin and tetracycline): enzymes; vitamins (e.g., riboflavin, B12, beta-carotene); and hormones. Preferred fermentation processes include alcohol fermentation processes, as are well known in the art. Preferred fermentation processes are anaerobic fermentation processes, as are well known in the art.

Processes for Producing Fermentation Products from Un-gelatinized Starch-containing In this aspect the invention relates to processes for producing a fermentation product from starch-containing material without gelatinization of the starch-containing material. In one embodiment only a glucoamylase of the invention is used during saccharification and fermentation. According to the invention the desired fermentation product, such as ethanol, can be produced without liquefying the aqueous slurry containing the starch-containing material. In one embodiment a process of the invention includes saccharifying (milled) starch-containing material e.g., granular starch, below the gelatinization temperature in the presence of a glucoamylase of the invention to produce sugars that can be fermented into the desired fermentation product by a suitable fermenting organism.

Example 4 below discloses production of ethanol from un-gelatinized (uncooked) milled corn using glucoamylases of the invention derived from *Peniphora rufomarginata* for one-step fermentation alone and in combination with an alpha-amylase.

Accordingly, in this aspect the invention relates to a process for producing a fermentation product from starch-containing material comprising:

(a) saccharifying starch-containing material with a glucoamylase having the sequence shown as amino acids 1 to 558 in SEQ ID NO: 2, or a glucoamylase having at least 60% identity thereto, at a temperature below the initial gelatinization temperature of said starch-containing material, (b) fermenting using a fermenting organism.

Steps (a) and (b) of the process of the invention may be carried out sequentially or simultaneously. In an embodiment a slurry comprising water and starch-containing material is prepared before step (a).

The fermentation process may be carried out for a period of 1 to 250 hours, preferably is from 25 to 190 hours, more preferably from 30 to 180 hours, more preferably from 40 to 170 hours, even more preferably from 50 to 160 hours, yet more preferably from 60 to 150 hours, even yet more preferably from 70 to 140 hours, and most preferably from 80 to 130 hours.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein. S. and Lii. C., Starch/Stärke, Vol. 44 (12) pp, 461-466 (1992).

Before step (a) a slurry of starch-containing material, such as granular starch, having 10-55 wt.-% dry solids, preferably 25-40 wt.-% dry solids, more preferably 30-35% dry solids of starch-containing material may be prepared. The slurry may include water and/or process waters, such as stillage (backset), scrubber water, evaporator condensate or distillate, side stripper water from distillation, or other fermentation product plant process water. Because the process of the invention is carried out below the gelatinization temperature and thus no significant viscosity increase takes place, high levels of stillage may be used if desired. In an embodiment the aqueous slurry contains from about 1 to about 70 vol.-% stillage, preferably 15-60% vol.-% stillage, especially from about 30 to 50 vol.-% stillage.

The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the starch-containing material is converted into a soluble starch hydrolysate.

The process of the invention is conducted at a temperature below the initial gelatinization temperature. Preferably the temperature at which step (a) is carried out is between 30-75° C., preferably between 45-60° C.

In a preferred embodiment step (a) and step (b) are carried out as a sequential or simultaneous saccharification and fermentation process. In such preferred embodiment the process is typically carried at a temperature between 25° C. and 40° C., such as between 29° C. and 35° C., such as between 30° C. and 34° C., such as around 32° C. According to the invention the temperature may be adjusted up or down during fermentation.

In an embodiment simultaneous saccharification and fermentation is carried out so that the sugar level, such as glucose level, is kept at a low Level such as below 6 wt.-%, preferably below about 3 wt.-%, preferably below about 2 wt.-%, more preferred below about 1 wt.-%., even more preferred below about 0.5%, or even more preferred 0.25% wt.-%, such as below about 0.1 wt.-%. Such low levels of sugar can be accomplished by simply employing adjusted quantities of enzyme and fermenting organism. A skilled person in the art can easily determine which quantities of enzyme and fermenting organism to use. The employed quantities of enzyme and fermenting organism may also be selected to maintain low concentrations of maltose in the fermentation broth. For instance, the maltose level may be kept below about 0.5 wt.-% or below about 0.2 wt.-%.

The process of the invention may be carried out at a pH in the range between 3 and 7, preferably from pH 3.5 to 6, or more preferably from pH 4 to 5.

Starch-containing Materials

Any suitable starch-containing starting material, including granular starch, may be used according to the present invention. The starting material is generally selected based on the desired fermentation product. Examples of starch-containing starting maters, suitable for use in a process of present invention, include tubers, roots, sterns, whole grains, corns, cobs, wheat, barley, rye, milo, sago, cassava, tapioca, sorghum, rice peas, beans, or sweet potatoes, or mixtures thereof, or cereals, sugar-containing raw materials, such as molasses, fruit materials, sugar cane or sugar beet, potatoes, and cellulose-containing materials, such as wood or plant residues, or mixtures thereof. Contemplated are both waxy and non-waxy types of corn and barley.

The term "granular starch" means raw uncooked starch, i.e., starch in its natural form found in cereal, tubers or grains. Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch containing material comprising milled whole grain including non-starch fractions such as germ residues and fibers. The raw material, such as whole grain, is milled in order to open up the structure and allowing for further processing. Two milling processes are preferred according to the invention: wet and dry milling. In dry milling whole kernels are milled and used. Wet milling gives a good separation of germ and meal (starch granules and protein) and is often applied at locations where the starch hydrolysate is used in production of syrups. Both dry and wet milling is well known in the art of starch processing and is equally contemplated for the process of the invention.

The starch-containing material is reduced in particle size, preferably by dry or wet milling, in order to expose more surface area. In an embodiment the particle size is between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen.

Fermentation Products

The term "fermentation product" means a product produced by a process including a fermentation step using a fermenting organism. Fermentation products contemplated according to the invention include alcohols (e.g. ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin. $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes, as are well known in the art. Preferred fermentation processes are anaerobic fermentation processes, as are well known in the art.

Fermenting Organisms

"Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include fungal organisms, such as yeast. Preferred yeast includes strains of *Saccharomyces* spp., in particular, *Saccharomyces cerevisiae*. Commercially available yeast include, e.g., Red Star™/ Lesaffre Ethanol Red (available from Red Star/Lesaffre, USA) FALI (available from Fleischmann's Yeast, a division of Burns Philp Food inc., USA), SUPERSTART (available from Alltech), GERT STRAND (available from Gert Strand AB, Sweden) and FERMIOL (available from DSM Specialties).

Enzymes

Glucoamylase

The glucoamylase is preferably a glucoamylase of the invention. However, as mentioned above a glucoamylase of the invention may also be combined with other glucoamylases.

The glucoamylase may added in an amount of 0.001 to 10 AGU/g DS, preferably from 0.01 to 5 AGU/g DS, such as around 0.1, 0.3, 0.5, 1 or 2 AGU/g DS, especially 0.1 to 0.5 AGU/g DS or 0.02-20 AGU/g DS, preferably 0.1-10 AGU/g DS.

Alpha-Amylase

The alpha-amylase may according to the invention be of any origin. Preferred are alpha-amylases of fungal or bacterial origin.

In a preferred embodiment the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention a bacterial alpha-amylase may preferably be derived from the genus *Bacillus*.

In a preferred embodiment the *Bacillus* alpha-amylase is derived from a strain of *B. licheniformis, B. amyloliquefaciens, B. subtilis* or *B. stearothermophilus*, but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NOS: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or 6,187,576 (hereby incorporated by reference) and include *Bacillus stearothermophilus* alpha-amylase (BSG alpha-amylase) variants having a deletion of one or two amino acid in position 179 to 182, preferably a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO: 3 disclosed in WO 99/19467 or deletion of amino acids 179 and 180 using SEQ ID NO: 3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta(181-182) and further comprise a N193F substitution (also denoted I181*+G182*+N193F) compared to the wild-type BSG alpha-amylase amino acid sequence set forth in SEQ ID NO: 3 disclosed in WO 99/19467.

The alpha-amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown as SEQ ID NO: 4 in WO 99/19467) and the 37 N-terminal amino acid residues of the alpha-amylase derived from *Bacillus amyloliquefaciens* (shown as SEQ ID NO: 3 in WO 99/194676), with one or more, especially all, of the following substitution:

G48A+T49I+G107A+H156Y+A181T+N190F+I201F+A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

The bacterial alpha-amylase may be added in amounts as are well-known in the art. When measured in KNU units (described below in the "Materials & Methods"-section) the alpha-amylase activity is preferably present in an amount of 0.5-5,000 NU/9 of DS, in an amount of 1-500 NU/g of DS, or more preferably in an amount of 5-1,000 NU/g of DS, such as 10-100 NU/g DS.

Fungal Alpha-Amylases

Fungal acid alpha-amylases include acid alpha-amylases derived from a strain of the genus *Aspergillus*, such as *Aspergillus oryzae*, *Aspergillus niger*, or *Aspergillus kawachii* alpha-amylases.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

In a preferred embodiment the alpha-amylase is derived from *Aspergillus kawachii* and disclosed by Kaneko et al. J. Ferment. Bioeng. 81:292-298 (1996) "Molecular-cloning and determination of the nucleotide-sequence of a gene encoding an acid-stable alpha-amylase from *Aspergillus kawachii*"; and further as EMBL:#A6008370.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid alpha-amylase is derived from a strain of *Aspergillus kawachii*.

Fungal Hybrid Alpha-Amylases

In a preferred embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM) and optional a linker.

Specific examples of contemplated hybrid alpha-amylases include those disclosed in U.S. patent application No. 60/638, 614 including Fungamyl variant with catalytic domain JA118 and *Athelia rolfsii* SBD (SEQ ID NO: 100 in U.S. application No. 60/638,614). *Rhizomucor pusillus* alpha-amylase with *Athelia rolfsii* AMG linker and SBD (SEQ ID NO: 101 in U.S. application No. 60/638,614) and *Meripilus giganteus* alpha-amylase with *Athelia rolfsii* glucoamylase linker and SBD (SEQ ID NO: 102 in U.S. application no. 60/638,614).

Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCOLASE from DSM (Gist Brocades), BAN™, TERMAMYL™ SC, FUNGAMYL™, LIQUOZYME™ X and SAN™ SUPER, SANT™ EXTRA L (Novozymes A/S) and CLARASE™ L-40,000. DEX-LO™, SPEZYME™ FRED, SPEZYE™ AA, SPEZYME™ Ethyl, and SPEZYME™ DELTA AA (Genencor Int.), and the acid fungal alpha-amylase sold under the trade name SP288 (available from Novozymes NS, Denmark).

An acid alpha-amylases may according to the invention be added in an amount 0.1 to 10 AFAU/g DS, preferably 0.10 to 5 AFAU/g DS, especially 0.3 to 2 AFAU/g DS.

Production of Syrup

The present invention also provides a process of using a glucoamylase of the invention for producing syrup, such as glucose and the like, from starch-containing material. Suitable starting materials are exemplified in the "Starch-containing materials"-section above. Generally, the process comprises the steps of partially hydrolyzing starch-containing material (liquefaction) in the presence of alpha-amylase and then further saccharifying the release of glucose from the non-reducing ends of the starch or related oligo- and polysaccharide molecules in the presence of glucoamylase of the invention.

Liquefaction and saccharification may be carried our as described above for fermentation product production.

The glucoamylase of the invention may also be used in immobilized form. This is suitable and often used for producing specialty syrups, such as maltose syrups, and further for the raffinate stream of oligosaccharides in connection with the production of fructose syrups, e.g., high fructose syrup (HFS).

Consequently, this aspect of the invention relates to a process of producing syrup from starch-containing material, comprising (a) liquefying starch-containing material in the presence of an alpha-amylase, (b) saccharifying the material obtained in step (a) using a glucoamylase of the invention.

A syrup may be recovered from the saccharified material obtained in step (b).

Details on suitable conditions can be found above.

Brewing

A glucoamylase of the invention can also be used in a brewing process. The glucoamylases of the invention is added in effective amounts which can be easily determined by the skilled person in the art.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and de-scribed herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties. The present invention is further described by the following examples which should not be construed as limiting the scope of the invention.

Materials & Methods

Glucoamylases:

Glucoamylase AN: Glucoamylase derived from *Aspergillus niger* disclosed in (Boel et al. (1984), EMBO J. 3 (5) p. 1097-1102) and available from Novozymes NS, Denmark.

Alpha-Amylase:

Alpha-Amylase A: Hybrid alpha-amylase consisting of *Rhizomucor pusillus* alpha-amylase (SEQ ID NO: 6 herein) with *Aspergillus niger* glucoamylase linker (SEQ ID NO: 8 herein) and BD (SEQ ID NO: 10 herein) disclosed as V039 in Table 5 in co-pending International Application no. PCT/US05/46725 (WO 2006/069290).

Yeast RED STAR™ available from Red Star/Lesaffre, USA

Other Materials pENI2516 is described in WO 2004/069872.

*Aspergillus niger* MBin118 is disclosed in WO 2004/090155 (see e.g., Example 11)

Deposit of Biological Material

The following biological material has been deposited under the terms of the Budapest Treaty at Deutshe Sammmlung von Microorganismen and Zellkulturen GmbH (DSMZ), Mascheroder Weg 1b, D-38124 Braunschweig DE, and given the following accession number:

| Deposit | Accession Number | Date of Deposit |
| --- | --- | --- |
| *Escherichia coli* NN49873 | DSM 18150 | 3 Apr. 2006 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Media and Reagents:

Chemicals used as buffers and substrates were commercial products of at least reagent grade.

PDA: 39 g/L Potato Dextrose Agar, 20 g/L agar, 50 ml/L glycerol

Methods

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al (eds.) "Current protocols in Molecular Biology", John Wiley and Sons, 1995; Harwood, C. R., and Cutting, S. M. (eds.) "Molecular Biological Methods for *Bacillus*". John Wiley and Sons, 1990.

Glucoamylase Activity

Glucoamylase activity may be measured in AGI units or in Glucoamylase Units (AG U).

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch—Glucoamylase Method with Subsequent Measurement of Glucose with Glucose Oxidase in "Approved methods of the American Association of Cereal Chemists", Vol. 1-2 AACC, from American Association of Cereal Chemists, (2000); ISBN: 1-891127-12-8.

One glucoamylase unit (AGI) is the quantity of enzyme which will form 1 micro mole of glucose per minute under the standard conditions of the method.

Standard Conditions/Reaction Conditions:

| | |
|---|---|
| Substrate: | Soluble starch, concentration approx. 16 g dry matter/L. |
| Buffer: | Acetate, approx. 0.04 M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH ~9) |
| Enzyme concentration: | 0.15-0.55 AAU/mL. |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |

| Color reaction: | |
|---|---|
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-amylase Activity (KNU)

The alpha-amylase activity may be determined using potato starch as substrate. This method is based on the breakdown of modified potato starch by the enzyme, and the reaction is followed by mixing samples of the starch/enzyme solution with an iodine solution, Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M Ce; and pH 5.6) dextrinizes 5260 mg starch dry substance Merck Amylum solubile.

A folder EB-SM-0009.02/01 describing this analytical method in more detail is available upon request to Novozymes ALS, Denmark, which folder is hereby included by reference.

Acid Alpha-amylase Activity

When used according to the present invention the activity of any acid alpha-amylase may be measured in AFAU (Acid Fungal Alpha-amylase Units). Alternatively activity of acid alpha-amylase may be measured in MU (Acid Alpha-amylase Units).

Acid Alpha-amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard Conditions/Reaction Conditions:

| | |
|---|---|
| Substrate: | Soluble starch. Concentration approx. 20 g DS/L. |
| Buffer: | Citrate, approx. 0.13 M, pH = 4.2 |
| Iodine solution: | 40.176 g potassium iodide + 0.088 g iodine/L |
| City water | 15°-20° dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine. Further details can be found in EP 0140410 B2, which disclosure is hereby included by reference.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

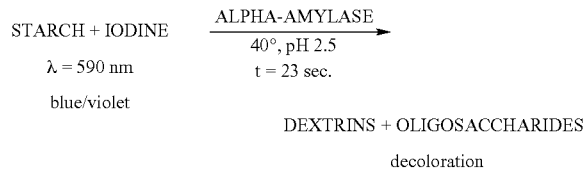

Standard Conditions/Reaction Conditions:

| | |
|---|---|
| Substrate: | Soluble starch, approx. 0.17 g/L |
| Buffer: | Citrate, approx. 0.03 M |
| Iodine (I2): | 0.03 g/L |
| CaCl2: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

EXAMPLES

Example 1

DNA Extraction and PCR Amplification of *Peniophora rufomarginata* Glucoamylase Gene Aerial hyphae of *Peniophora rufomarginata* growing on a PDA (Potatoe Dextrose Agar) plate were scraped off the plate and used for genomic DNA extraction using FastDNA SPIN Kit for Soil (Qbiogene, USA) according to the manufacturer's instructions.

PCR reaction was done on genome DNA with the degenerated primers EuAMF1 and EuAMR4:

```
                                         (SEQ ID NO: 11)
EuAMF1   5'-ACGTACGGATCCAYTWCTAYWCBTGGACHCGYGA-3'

(SEQ ID NO: 12)
EuAMR4   5'-GTACGTAAGCTTRTCYTCRGGGTAVCGDCC-3'
```

Where D=A or G or T; R=A or G; S=C or G; V=A or C or G; Y=C or T; W=A or T; B=G or C or T; H=A or T or C The amplification reaction (13 microL) was composed of 1 microL genome DNA solution, 1 microM primer EuAMF1 (25 pmol/microL), 1 microM primer EuAMR4 (25 pmol/microL), 11 microL Extensor Hi-Fidelity PCR Master Mix (ABgene, UK). The reaction was incubated in a DNA Engine Dyad PTC-0220 (MJ Research, USA) programmed as follows: 1 cycle at 94° C. for 5 minutes; 20 cycles each at 94° C. for 45 seconds, 65° C. for 45 seconds, with an annealing temperature decline of 1° C. per cycle, and 72° C. for 1 minute; followed by 20 cycles at 94° C. for 45 seconds. 48° C. for 45 seconds and 72° C. for 1 minute; 1 cycle at 72° C. for 7 minutes; and a hold at 4° C. The PCR product was purified using ExoSAP-IT (USB, USA) according to the manufacturer's instructions and sequenced using the primers as used in the amplification reaction. The sequence was subsequently compared to the *Aspergillus niger* glucoamylase gene, showing that the PCR product encoded a part of a glucoamylase.

Example 2

Cloning of Glucoamylase Gene from *Peniophora rufomarginata*

From the partial sequence of the *Peniophora rufomarginata* glucoamylase more gene sequence was obtained with PCR based gene walking using the Vectorette Kit from SIGMA-Genosys. The gene walking was basically done as described in the manufacturer's protocol. 0.15 micro g genomic DNA of *Peniophora rufomarginata* was digested with EcoRI. BamHI, HindIII, and ClaI independently. The digested DNA was ligated with the corresponding Vectorette units supplied by the manufacture using a DNA Engine Dyad PTC-0220 (MJ Research, USA) programmed as follows: 1 cycle at 16° C. for 60 minutes: 4 cycles each at 37° C. for 20 minutes, 16° C. for 60 minutes. 37° C. for 10 minutes: followed by 1 cycle at 16° C. for 60 minutes and a hold at 4° C. The ligation reactions were subsequent diluted 5 times with sterile water.

PCR reactions with the linker-ligated genome DNA of the *Peniophora rufomarginata* as template was performed with a DNA Engine Dyad PTC-0220 (MJ Research, USA) programmed as follows: 1 cycle at 94° C. for 5 minutes; 40 cycles each at 94° C. for 15 seconds, 72° C. for 1 minute, 72° C. for 1 minute, 1 cycle at 72° C. for 7 minutes; and a hold at 4° C. using the supplied Vectorette primer and the specific *Peniophora rufomarginata* AMG primers 50311F1 and 50311R2, respectively, as shown below.

```
50311F1:
5'-CGATTCACACCTGGGACATCAAGG-3'    (SEQ ID NO: 13)

50311R2:
5'-AAGACACAGTACCAGACGGGTTGG-3'    (SEQ ID NO: 14)
```

The amplification reactions (12.5 microL) were composed of 0.5 microL of linker-ligated genome DNAs, 400 nM Vectorette primer, 400 nM *Peniophora rufomarginata* specific primer, 11 microL Extensor Hi-Fidelity PCR Master Mix (ABgene, UK). After the PCR reaction the PCR products were purified using ExoSAP-IT (USB, USA) according to the manufacturers instructions and sequenced and subsequently compared to the *Aspergillus niger* glucoamylase gene.

A 1.5 kb amplified band was obtained by the PCR reaction from BamHI digested genome DNA amplified with the primer 50311R2. Sequencing of the PCR product using this primer showed that it encoded the remaining 350 basepairs of the glucoamylase gene in the 5' direction (N-terminal of the encoded protein).

A 1.1 amplified band was obtained by the PCR reaction from ClaI digested genome DNA amplified with the primer 50311F1. Sequencing of the PCR product using this primer showed that it encoded further 550 basepairs of the glucoamylase gene in the 3' direction, however not reaching the end of the gene. Therefore, an additional sequencing primer 50311F2, were designed based on the newly obtained additional sequence of the glucoamylase gene. A new DNA-Vectorette ligation and following amplification set up as described above was set up. A 2 kb PCR product obtained from the HindIII digested genome ligation was sequenced with the 50311F2 primer, and was shown to encode the remaining part of the glucoamylase gene in the 3' direction (C-terminal of the encoded protein).

```
50311F2
5' GGTGGCAGCACCGTCGCTGTAACC    (SEQ ID NO: 15)
```

Example 3

Expression of the Glucoamylase Gene from *Peniophora rufomarginata*

The glucoamylase gene from *Peniophora rufomarginata* was cloned by PCR using gDNA as template, Reddy PCR Master Mix (ABgene, UK) and the primers 50311F3 and 50311R3 as shown below:

```
50311F3:
                                 (SEQ ID NO: 16)
5' CAGCACGGATCCAAGATGCGTCTCCCACAACTTG 3'

50311R3
                                 (SEQ ID NO: 17)
5' GCATCAAGGCGGCCGCCTAGCGCCAGGAATCGTTGGC 3'
```

Primer 50311F3 and 50311R3 introduced a BamHI and NotI restrictions site in the amplified DNA fragment and it was subsequently ligated into the BamHI and NotI restrictions site of the *Aspergillus* expression vector pENI2516. The ligation mixture was transformed into *E. coli* TOP10 (Invitrogen, USA) to create the expression plasmid pENI2516AMGNN50311E1. The amplified plasmid was recovered using a QIAprep Spin Miniprep kit (QIAGEN, USA) according to the manufacturer's instructions.

The glucoamylase of pENI2516AMGNN50311E1 was sequenced. Unfortunately, a PCR error occurred in the coding region of the glucoamylase gene. The PCR error was removed by a second cloning step as described below.

Two PCR reactions were performed. PCR reaction 1 contained 10 ng/microL pENI2516AMGNN50311E1 as template, 0.2 mM dNTP, 1× buffer, 1.5 mM MgCl$_2$, 1 unit DyNAzyme EXT (New England Biolabs, UK), and 1 pmol/microL of each of the primers NN50311fw1 and NN50311bw2 (see below). The total volume was 50 microL.

```
                                 (SEQ ID NO: 18)
NN50311fw1: 5' GCGGATCCACCATGCGTCTCCCACAACTTGGAGTC (SEQ ID NO: 19)
NN50311bw2: 5' AGCTTGATTACGGGCCAGAGCGTGTTCGTGAC
```

PCR reaction 2 contained 10 ng/microL pENI2516AMGNN50311E1 as template. 0.2 mM dNTP, 1× buffer, 1.5 mM MgCl$_2$, 1 unit DyNAzyme EXT (New England Biolabs, UK) and 1 pmol/microL of each of the primers NN50311fw2 and NN50311bw1 (see below). The total volume was 50 microL.

```
                                 (SEQ ID NO: 20)
NN50311fw2: 5' CGAACACGCTCTGGCCCGTAATCAAGCTTG (SEQ ID NO: 21)
NN50311bw1: 5' GGGCGGCCGCTAGCGCCAGGAATCGTTGGCAGTA
```

Both PCR reaction 1 and PCR reaction 2 were performed with a DNA Engine Dyad PTC-0220 (MJ Research, USA) programmed as follows: 1 cycle at 94° C. for 3 minutes; 15 cycles each at 94° C. for 20 seconds, 54° C. for 20 seconds and 72° C. for 1 minute. 1 cycle at 72° C. for 5 minutes.

A 0.7 kbp DNA band and a 1.5 kbp DNA band was purified from PCR reaction 1 and PCR reaction 2, respectably, using GFX PCR DNA Gel Band Purification Kit (Amersham Biosciences, UK).

A third PCR reaction was done containing 1 micro gram of the purified 0.7 kbp DNA band and 1 micro gram of the purified 1.5 kbp DNA band as template, 0.2 mM dNTP, 1× buffer, 1.5 mM MgCl$_2$, 1 unit DyNAzyme EXT (New England Biolabs, UK) and 1 pmol/microL of each of the primers NN50311fw1 (SEQ ID NO: 20) and NN50311bw1 (SEQ ID NO: 21). The total volume was 50 microL. The PCR reaction was performed with a DNA Engine Dyad PTC-0220 (MJ Research, USA) programmed as follows: 1 cycle at 94° C. for 3 minutes; 9 cycles each at 94° C. for 20 seconds, 54° C. for 20 seconds and 72° C. for 2 minute, 1 cycle at 72° C. for 5 minutes. The DNA was purified from the PCR reaction using GFX PCR DNA Gel Band Purification Kit (Amersham Biosciences, UK) and subsequently digested with BamHI and NotI and ligated into the BamHI and NotI restrictions site of the *Aspergillus* expression vector pENI2516. The ligation mixture was transformed into *E. coli* TOP10 (Invitrogen, USA) to create the expression plasmid pENI2516AMGNN50311. The amplified plasmid was recovered using JETQUICK Plasmid Miniprep Spin Kit 50 (Genomed, Germany) according to the manufacturer's instructions.

The glucoamylase gene of pENI2516AMGNN50311 was sequenced and verified to be identical to the genome sequence.

pENI2516AMGNN50311 was transformed into *Aspergillus niger* MBin118 and the glucoamylase expressed using standard method well known in the art.

Example 4

Yeast Propagation

Yeast was propagated prior to fermentation. Corn (yellow dent No. 2) was ground to pass through #45 mesh screen. 200 ml tap water and 1 g urea were mixed with 300 g corn mash. Penicillin was added to 3 mg/liter. In 50 g of the mash slurry, 6.4 microL Glucoamylase AN and 0.024 g dry yeast (from RED START) were added and the pH was adjusted to 5.0. The yeast slurry was incubated at 32° C. with constant stirring at 300 rpm for 7 hours in a partially open flask.

One-Step Fermentation Using *Peniophora rufomarginata* Glucoamylase

All one step ground corn to ethanol treatments were evaluated via mini-scale fermentations. Briefly, 410 g of ground yellow dent corn (with particle size around 0.5 mm) was added to 590 g tap water. This mixture was supplemented with 3.0 ml 1 g/L penicillin and 1 g of urea. The pH of this slurry was adjusted to 4.5 with 5 N NaOH. DS level was determined to be around 35 wt, % (The actual DS was measured with an IR-200 moisture analyzer from Denver Instrument Co.). Approximately 5 g of this slurry was added to 20 ml vials. Each vial was dosed with the appropriate amount of enzyme followed by addition of 200 micro liters yeast propagate per 5 g slurry. Actual enzyme dosages were based on the exact weight of corn slurry in each vial, Vials were closed and incubated at 32° C. immediately. 9 replicate fermentations of each treatment were run. Three replicates were selected for 24 hours, 48 hours and 70 hours time point analysis. Vials were vortexed at 24, 48 and 70 hours and analyzed by HPLC. The HPLC preparation consisted of stopping the reaction by addition of 50 microliters of 40% $H_2SO_4$, centrifuging, and filtering through a 0.45 micrometer filter. Samples were stored at 4° C. prior to analysis.

Agilent™ 1100 HPLC system coupled with RI detector was used to determine ethanol and sugars. The HPLC system consists of a degasser, quat-pump, cooled autosampler and heated column compartment. The separation column was aminex HPX-87H ion exclusion column (300 mm×7.8 mm) from BioRad™, which links to 30 mm×4.6 mm micro-guard cation-H cartridge guard column. 10 microL sample was injected at the flow rate of 0.6 ml/min. The mobile phase was 5 mM $H_2SO_4$. The column was kept at 65° C. and RI detector at 50° C. The total run time was 25 min per sample.

The results are shown in the table below. Increase of *P. rufomarginata* glucoamylase results in increase of ethanol yield. High ethanol yield is achieved when *P. ruformarginata* glucoamylase is used together with alpha-amylase Alpha-Amylase A in one step corn to ethanol process.

|   | *P. rufomarginata* AMG (mg enzyme/g DS) | Alpha-Amylase A (mg enzyme/g DS) | Ethanol (% w/v) | | |
|---|---|---|---|---|---|
|   |   |   | 24 hours | 48 hours | 70 hours |
| 1 | 0 | — | 1.75 | 2.07 | 2.34 |
| 2 | 0.02 | — | 2.47 | 3.52 | 4.55 |
| 3 | 0.04 | — | 2.98 | 4.25 | 5.62 |
| 4 | 0.08 | — | 3.79 | 5.75 | 7.28 |
| 5 | 0 | 0.04 | 6.78 | 10.90 | 13.25 |
| 6 | 0.02 | 0.04 | 7.47 | 11.72 | 13.57 |
| 7 | 0.04 | 0.04 | 7.77 | 12.49 | 14.66 |
| 8 | 0.08 | 0.04 | 8.46 | 13.14 | 15.50 |

The invention claimed is:

1. An isolated polypeptide having glucoamylase activity, selected from the group consisting of:
   (a) a polypeptide which has at least 95% identity with the sequence of amino acids 1 to 558 of SEQ ID NO: 2;
   (b) a polypeptide which is encoded by a nucleotide sequence which hybridizes under high stringency conditions with the complementary strand of (i) the sequence of nucleotides 61 to 2301 of SEQ ID NO: 1, or (ii) the sequence of nucleotides 61 to 1734 of SEQ ID NO: 3, wherein the high stringency conditions are defined as prehybridization and hybridization at 42° C. in 5×SSPE, 0.3% SDS, 200 micrograms/ml sheared and denatured salmon sperm DNA, and 50% formamide followed by washing three times each for 15 minutes using 2×SSC, 0.2% SDS at 65° C.; and
   (c) a fragment of the sequence of amino acids 1 to 558 of SEQ ID NO: 2, which has glucoamylase activity.

2. The polypeptide of claim 1, which has at least 95% identity with the sequence of amino acids 1 to 558 of SEQ ID NO: 2.

3. The polypeptide of claim 1, which has at least 97% identity with the sequence of amino acids 1 to 558 of SEQ ID NO: 2.

4. The polypeptide of claim 1, which comprises the sequence of amino acids 1 to 558 of SEQ ID NO: 2.

5. The polypeptide of claim 1, which is encoded by a nucleotide sequence which hybridizes under high stringency conditions with the complementary strand of (i) the sequence of nucleotides 61 to 2301 of SEQ ID NO: 1, or (ii) the sequence of nucleotides 61 to 1734 of SEQ ID NO: 3, wherein the high stringency conditions are defined as prehybridization and hybridization at 42° C. in 5×SSPE, 0.3% SDS, 200 micrograms/ml sheared and denatured salmon sperm DNA, and 50% formamide followed by washing three times each for 15 minutes using 2×SSC, 0.2% SDS at 65° C.

6. The polypeptide of claim 1, which is encoded by a nucleotide sequence which hybridizes under very high stringency conditions with the complementary strand of (i) the sequence of nucleotides 61 to 2301 of SEQ ID NO: 1, or (ii) the sequence of nucleotides 61 to 1734 of SEQ ID NO: 3, wherein the high stringency conditions are defined as prehybridization and hybridization at 42° C. in 5×SSPE, 0.3% SDS, 200 micrograms/ml sheared and denatured salmon sperm DNA, and 50% formamide followed by washing three times each for 15 minutes using 2×SSC, 0.2% SDS at 70° C.

7. The polypeptide of claim 1, which is a fragment of the sequence of amino acids 1 to 558 of SEQ ID NO: 2, which has glucoamylase activity.

8. A composition comprising a glucoamylase of claim 1 and an alpha-amylase.

9. A process for producing a fermentation product, comprising:
   (a) liquefying a starch-containing material with an alpha-amylase to form a liquefied material;
   (b) saccharifying the liquefied material using a glucoamylase of claim 1 to form a saaccharified material;
   (c) fermenting the saccharified material using a fermenting organism.

10. A process for producing a fermentation product comprising:
    (a) saccharifying a starch-containing material with a glucoamylase of claim 1 at a temperature below the initial gelatinization temperature of said starch-containing material; and
    (b) fermenting the saccharified material using a fermenting organism.

11. The process of claim 10, wherein steps (a) and (b) are carried out sequentially or simultaneously.

12. The process of claim 10, wherein an alpha-amylase is present during saccharification.

13. A process of producing syrup from starch-containing material, comprising
    (a) liquefying starch-containing material, in the presence of an alpha-amylase, (b) saccharifying the material obtained in step (a) using a glucoamylase of claim 1.

14. The process of claim 13, further comprising refining, conversion and/or recovery of the syrup.

15. An isolated polypeptide having glucoamylase activity, selected from the group consisting of:
(a) a polypeptide which has at least 95% identity with the sequence of amino acids 1 to 448 of SEQ ID NO: 2;
(b) a polypeptide which is encoded by a nucleotide sequence which hybridizes under high stringency conditions with the complementary strand of (i) the sequence of nucleotides 61 to 1844 of SEQ ID NO: 1, or (ii) the sequence of nucleotides 61 to 1449 of SEQ ID NO: 3, wherein the high stringency conditions are defined as prehybridization and hybridization at 42° C. in 5×SSPE, 0.3% SDS, 200 micrograms/ml sheared and denatured salmon sperm DNA, and 50% formamide followed by washing three times each for 15 minutes using 2×SSC, 0.2% SDS at 65° C.; and
(c) a fragment of the sequence of amino acids 1 to 448 of SEQ ID NO: 2, which has glucoamylase activity.

16. The polypeptide of claim 15, which has at least 95% identity with the sequence of amino acids 1 to 448 of SEQ ID NO: 2.

17. The polypeptide of claim 15, which has at least 97% identity with the sequence of amino acids 1 to 448 of SEQ ID NO: 2.

18. The polypeptide of claim 15, which comprises the sequence of amino acids 1 to 448 of SEQ ID NO: 2.

19. The polypeptide of claim 15, which is encoded by a nucleotide sequence which hybridizes under high stringency conditions with the complementary strand of (i) the sequence of nucleotides 61 to 1844 of SEQ ID NO: 1, or (ii) the sequence of nucleotides 61 to 1449 of SEQ ID NO: 3, wherein the high stringency conditions are defined as prehybridization and hybridization at 42° C. in 5×SSPE, 0.3% SDS, 200 micrograms/ml sheared and denatured salmon sperm DNA, and 50% formamide followed by washing three times each for 15 minutes using 2×SSC, 0.2% SDS at 65° C.

20. The polypeptide of claim 15, which is encoded by a nucleotide sequence which hybridizes under very high stringency conditions with the complementary strand of (i) the sequence of nucleotides 61 to 1844 of SEQ ID NO: 1, or (ii) the sequence of nucleotides 61 to 1449 of SEQ ID NO: 3, wherein the high stringency conditions are defined as prehybridization and hybridization at 42° C. in 5×SSPE, 0.3% SDS, 200 micrograms/ml sheared and denatured salmon sperm DNA, and 50% formamide followed by washing three times each for 15 minutes using 2×SSC, 0.2% SDS at 70° C.

21. The polypeptide of claim 15, which is a fragment of the sequence of amino acids 1 to 448 of SEQ ID NO: 2, which has glucoamylase activity.

22. A composition comprising a glucoamylase of claim 15 and an alpha-amylase.

23. A process for producing a fermentation product, comprising:
(a) liquefying a starch-containing material with an alpha-amylase to form a liquefied material;
(b) saccharifying the liquefied material using a glucoamylase of claim 15 to form a saaccharified material;
(c) fermenting the saccharified material using a fermenting organism.

24. A process for producing a fermentation product comprising:
(a) saccharifying a starch-containing material with a glucoamylase of claim 15, at a temperature below the initial gelatinization temperature of said starch-containing material; and
(b) fermenting the saccharified material using a fermenting organism.

25. The process of claim 24, wherein steps (a) and (b) are carried out sequentially or simultaneously.

26. The process of claim 24, wherein an alpha-amylase is present during saccharification.

27. A process of producing syrup from starch-containing material, comprising
(a) liquefying starch-containing material, in the presence of an alpha-amylase,
(b) saccharifying the material obtained in step (a) using a glucoamylase of claim 15.

28. The process of claim 27, further comprising refining, conversion and/or recovery of the syrup.

29. An isolated polypeptide having carbohydrate-binding affinity, which comprises a carbohydrate-binding domain selected from the group consisting of:
(a) a carbohydrate-binding domain which has at least 95% identity with amino acids 464 to 558 of SEQ ID NO: 2;
(b) a carbohydrate-binding domain which is encoded by a nucleotide sequence which hybridizes under high stringency conditions with the complementary strand of (i) the sequence of nucleotides 1845 to 2301 of SEQ ID NO: 1, or (ii) the sequence of nucleotides 1450 to 1734 of SEQ ID NO: 3, wherein the high stringency conditions are defined as prehybridization and hybridization at 42° C. in 5×SSPE, 0.3% SDS, 200 micrograms/ml sheared and denatured salmon sperm DNA, and 50% formamide followed by washing three times each for 15 minutes using 2×SSC, 0.2% SDS at 65° C.; and
(c) a fragment of the sequence of amino acids 464 to 558 of SEQ ID NO: 2, which has carbohydrate-binding activity.

30. The polypeptide of claim 29, wherein the carbohydrate-binding domain has at least 95% identity with the sequence of amino acids 464 to 558 of SEQ ID NO: 2.

31. The polypeptide of claim 29, wherein the carbohydrate-binding domain has at least 97% identity with the sequence of amino acids 464 to 558 of SEQ ID NO: 2.

32. The polypeptide of claim 29, wherein the carbohydrate-binding domain comprises the sequence of amino acids 464 to 558 of SEQ ID NO: 2.

33. The polypeptide of claim 29, wherein the carbohydrate-binding domain is encoded by a nucleotide sequence which hybridizes under high stringency conditions with the complementary strand of (i) the sequence of nucleotides 1845 to 2301 of SEQ ID NO: 1, or (ii) the sequence of nucleotides 1450 to 1734 of SEQ ID NO: 3, wherein the high stringency conditions are defined as prehybridization and hybridization at 42° C. in 5×SSPE, 0.3% SDS, 200 micrograms/ml sheared and denatured salmon sperm DNA, and 50% formamide followed by washing three times each for 15 minutes using 2×SSC, 0.2% SDS at 65° C.

34. The polypeptide of claim 29, wherein the carbohydrate-binding domain is encoded by a nucleotide sequence which hybridizes under very high stringency conditions with the complementary strand of (i) the sequence of nucleotides 1845 to 2301 of SEQ ID NO: 1, or (ii) the sequence of nucleotides 1450 to 1734 of SEQ ID NO: 3, wherein the high stringency conditions are defined as prehybridization and hybridization at 42° C. in 5×SSPE, 0.3% SDS, 200 micrograms/ml sheared and denatured salmon sperm DNA, and 50% formamide followed by washing three times each for 15 minutes using 2×SSC, 0.2% SDS at 70° C.

35. The polypeptide of claim 29, wherein the carbohydrate-binding domain is a fragment of the sequence of amino acids 464 to 558 of SEQ ID NO: 2, which has carbohydrate-binding activity.

* * * * *

UNITED STATES PATENT AND TRADEMARK OFFICE
CERTIFICATE OF CORRECTION

PATENT NO. : 7,871,800 B2
APPLICATION NO. : 12/529582
DATED : January 18, 2011
INVENTOR(S) : Landvik et al.

Page 1 of 1

It is certified that error appears in the above-identified patent and that said Letters Patent is hereby corrected as shown below:

In claim 9 at column 64, line 49 delete "saaccharified" and insert -- saccharified --.

In claim 23 at column 65, line 57 delete "saaccharified" and insert -- saccharified --.

Signed and Sealed this
Twenty-second Day of March, 2011

David J. Kappos
*Director of the United States Patent and Trademark Office*